United States Patent
Chen et al.

(10) Patent No.: US 8,815,553 B2
(45) Date of Patent: Aug. 26, 2014

(54) ENGINEERING OF YEAST FOR CELLULOSIC ETHANOL PRODUCTION

(75) Inventors: Wilfred Chen, Rowland Heights, CA (US); Shen-Long Tsai, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 192 days.

(21) Appl. No.: 13/129,301

(22) PCT Filed: Nov. 14, 2009

(86) PCT No.: PCT/US2009/064491
§ 371 (c)(1),
(2), (4) Date: Aug. 29, 2011

(87) PCT Pub. No.: WO2010/057064
PCT Pub. Date: May 20, 2010

(65) Prior Publication Data
US 2011/0306105 A1 Dec. 15, 2011

Related U.S. Application Data

(60) Provisional application No. 61/115,068, filed on Nov. 15, 2008.

(51) Int. Cl.
*C12P 7/10* (2006.01)
*C12N 9/96* (2006.01)
*C12N 1/19* (2006.01)
*C12N 9/42* (2006.01)

(52) U.S. Cl.
CPC ............. *C12N 9/2437* (2013.01); *C12P 7/10* (2013.01); *Y02E 50/16* (2013.01); *Y02E 50/17* (2013.01)
USPC .................. 435/165; 435/188; 435/254.2

(58) Field of Classification Search
None
See application file for complete search history.

(56) References Cited

U.S. PATENT DOCUMENTS

| | | |
|---|---|---|
| 2003/0027298 A1 | 2/2003 | Bott et al. |
| 2008/0070791 A1 | 3/2008 | Morag |
| 2009/0035811 A1 | 2/2009 | Kohda et al. |

FOREIGN PATENT DOCUMENTS

| | | | |
|---|---|---|---|
| WO | WO 2008/100251 A1 * | 8/2008 | |
| WO | 2009/093118 A1 | 7/2009 | |
| WO | 2010/096562 A3 | 10/2010 | |

OTHER PUBLICATIONS

Lee R Lynd Consolidated bioprocessing of cellulosic biomass: an update Lee R Lynd. Current Opinion in Biotechnology 2005, 16:577-583.*

Yasuya Fujita Direct and Efficient Production of Ethanol from Cellulosic Material with a Yeast Strain Displaying Cellulolytic Enzymes Applied and Environmental Microbiology, Oct. 2002, p. 5136-5141.*

Edward A Bayer The potential of cellulases and cellulosomes for cellulosic waste management Current Opinion in Biotechnology 2007, 18:237-245.*

Bayer et al., "The cellulosome: multienzyme machines for degradation of plant cell wall polysaccharides," Annu. Rev. Microbiol., Jun. 11, 2004, pp. 521-554, vol. 58.

Bayer et al., "The potential of cellulases and cellulosomes for cellulosic waste managmenet," Current Opinion In Biotechnology, Apr. 25, 2007, pp. 237-245, vol. 18.

Fujita et al., "Synergistic Saccharification, and Direct Fermentation to Ethanol, of Amorphous Cellulose by Use of an Engineered Yeast Strain Codisplaying Three Types of Cellulolytic Enzyme," Applied and Environmental Microbiology, Feb. 2004, pp. 1207-1212, vol. 70, No. 2.

Mingardon et al., "Incorporation of Fungal Celluloases in Bacterial Minicellulosomes Yields Viable Synergistically Acting Cellulolytic Complex," Applied and Environmental Microbiology, Jun. 2007, pp. 3822-3832, vol. 73, No. 12.

Mingardon et al., "Exploration of new geometries in cellulosome-like chimeras," Applied and Environmental Microbiology, Sep. 28, 2007, pp. 7138-7149, Applied and Environmental Microbiology, vol. 73, No. 22.

Nordon et al., "Molecular engineering of the cellulosome complex for affinity and bioenergy applications," Biotechnology Letters, Dec. 31, 2008, pp. 465-476, vol. 31.

Tsai et al., "Functional assembly of mini-cellulosomes on the yeast surface for cellulose hydrolysis and ethanol production," Applied and Environmental Microbiology, Aug. 14, 2009, pp. 2-9.

Kim, Jung Hee, International Search Report and Written Opinion, PCT/US2009/064491, Korean Intellectual Property Office, Aug. 6, 2010.

Becamel, Philippe. International Preliminary Report on Patentability and Written Opinion. International Application No. PCT/US2009/064491. Date of Issuance of the Report: May 17, 2011.

Beguin, P., "Detection of Cellulase Activity in Polyacrylamide Gels Using Congo Red-Stained Agar Replicas," Anal.Biochem. 131(2):333-336 (1983).

Bowie et al., "Deciphering the Message in Protein Sequences: Tolerance to Amino Acid Substitutions," Science 247:1306-1310 (1990).

Casey et al., "A Convenient Domain Selection Marker for Gene Transfer in Industrial Strains of *Saccharomyces cerevisiae*: SMR1 Encoded Resistance to he Herbicide Sulfometuron Methyl," J. Inst. Brew 94(2):93-97 (1988).

(Continued)

*Primary Examiner* — Kagnew H Gebreyesus

(74) *Attorney, Agent, or Firm* — Joseph R. Baker, Jr.; Gavrilovich, Dodd & Lindsey LLP

(57) ABSTRACT

The disclosure provides designer cellulosomes for efficient hydrolysis of cellulosic material and more particularly for the generating of ethanol.

17 Claims, 7 Drawing Sheets

(56) References Cited

OTHER PUBLICATIONS

Caspi et al., "Conversion of Thermobifida fusca free exoglucanases into cellulosomal components: comparative impact on cellulose-degrading activity," J. Biotechnol. 135(4):351-357 (2008).

Cunningham et al., "High-Resolution Epitope Mapping of hGH-Receptor Interactions by Alanine-Scanning Mutagenesis," Science 244:1081-1085 (1989).

Den Haan et al., "Functional expression of cellobiohydrolases in *Saccharomyces cerevisiae* towards one-step conversion of cellulose to ethanol," Enzyme. Microb. Technol. 40(5):1291-1299 (2007).

Dijkerman et al., "The role of the cellulolytic high molecular mass (HMM) complex of the anaerobic fungus *Piromyces* sp. strain E2 in the hydrolysis of microcrystalline cellulose," Arch. Microbiol. 167(2-3):137-142 (1997).

Dijkerman et al., "Asorption Characteristics of Cellulolytic Enzymes from the Anaerobic Fungus *Piromyces* sp. strain E2 on Microcrystalline Cellulose," Appl. Environ. Microbiol. 62(1):20-5 (1996).

Fierobe et al., "Action of Designer Cellulosomes on Homogeneous Versus Complex Substrates," J. Biol. Chem. 280 (16):16325-16334 (2005).

Gal et al., "CelG from Clostridium cellulolyticum: A Multidomain Endoglucanase Acting Efficiently on Crystalline Cellulose," J. Bacteriol. 179(21):6595-6601 (1997).

Hahn-Hagerdal et al., "Metabolic Engineering of *Sacchromyces cerevisiae* for Xylose Utilization," Adv. Biochem Eng. Biotechnol. 73:53-84 (2001).

Ito et al., "Regulation of the Display Ratio of Enzymes on the *Saccharomyces cerevisiae* Cell Surface by the Immunoglobulin G and Cellulosomal Enzyme Binding Domains," Appl. Environ. Microbiol. 75(12):4149-4154 (2009).

Lamed et al., "Characterization of a Cellulose-Binding, Cellulase-Containing Complex in Clostridium thermocellum," J. Bacteriol. 156(2):282-836 (1983).

Levasseur et al., "Design and Production in *Aspergillus niger* of a Chimeric Protein Associating a Fugal Feruloyl Esterase and a Clostridial Dockerin Domain," Appl. Environ. Microbiol. 70(12):6984-6991 (2004).

Lynd et al., "Microbial Cellulose Utilization: Fundamentals and Biotechnology," Microbiol. Mol. Biol. Rev. 66 (3):506-577 (2002).

Ma et al., "Plasmid Construction by Homologous Recombination in Yeast," Gene 58(2-3):201-216 (1987).

McBride et al., "Utilization of cellobiose by recombinant beta-glucosidase-expressing strains of *Saccharomyces cerevisiae*:characterization and evaluation of the sufficiency of expression," Enzyme. Microb. Technol. 37(1):93-101 (2005).

Nagy et al., "Characterization of a double dockerin from the cellulosome of the anaerobic fungus *Piromyces equi*," J. Mol. Biol. 373(3):612-622 (2007).

Nakamura et al., "Codon Usage tabulated from the international DNA sequence databases: status for year 2000," Nucleic Acids Res. 28(1):292 (2000).

Raghothama et al., "Characterization of a cellulosome dockerin domain from the anaerobic fungus *Piromyces equi*," Nat. Struc. Biol. 8(9):775-779 (2001).

Schwikowski et al., "A network of protein-protein interaction in yeast," Nat. Biotechnol. 18(12):1257-1261 (2000).

Van Der Vaart et al., "Comparison of Cell Wall Proteins of *Saccharomyces cerevisiae* as Anchors for Cell Surface Expression of Heterologous Proteins," Appl. Environ. Microbiol. 63(2):615-620 (1997).

Van Resenburg et al., "Engineering Yeast for Efficient Cellulose Degradation," Yeast 14:67-76 (1998).

Van Rooyen et al., "Construction of cellobiose-growing and fermenting *Saccharomyces cerevisiae* strains," J. Biotech. 120:284-295 (2005).

Van Zyl et al., "Consolidated Bioprocessing for Bioethanol Production Using *Saccharomyces cerevisiae*," Adv. Biochem. Engin. Biotechnol. 37(1):125-129 (1992).

Wilson et al., "The anaerobic fungus Neocallimastix frontalis: Isolation and properties of a cellulosome-type enzyme fraction with the capacity to solubilize hydrogen-bond-ordered cellulose," Appl. Microbiol. Biotechno. 37(1):125-129 (1992).

\* cited by examiner

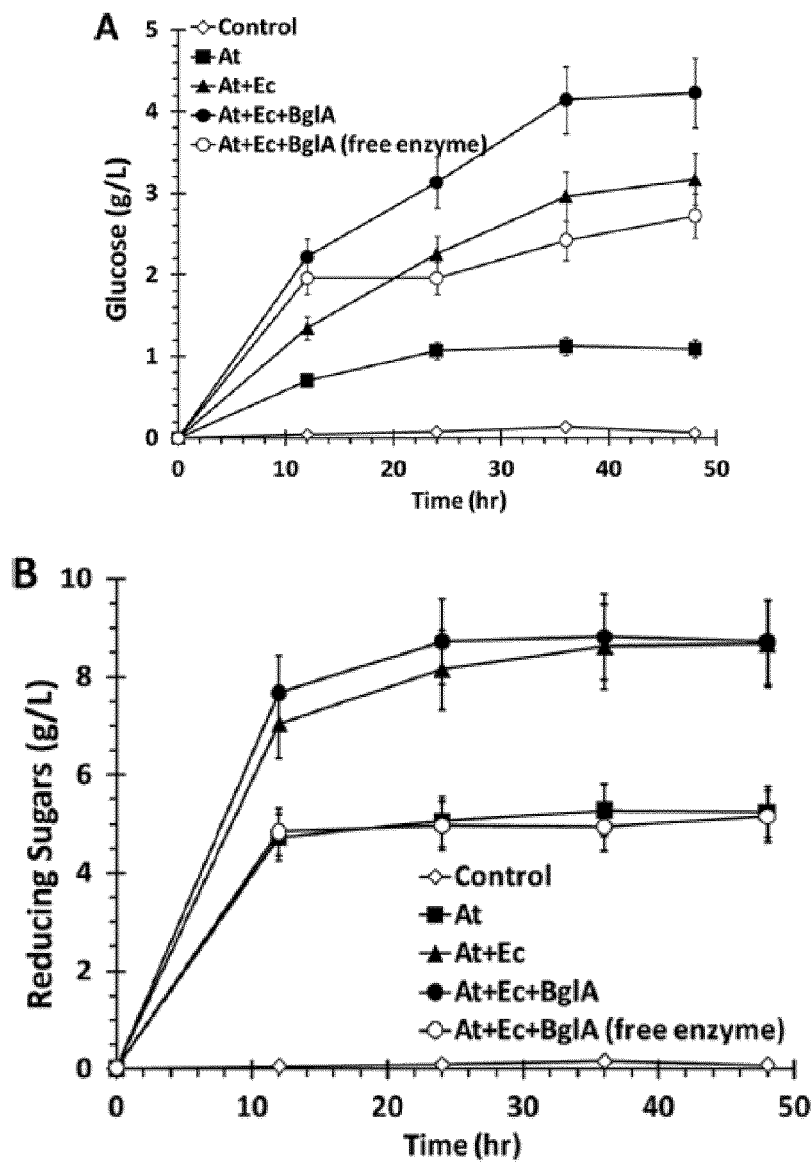
FIGURE 5A-B

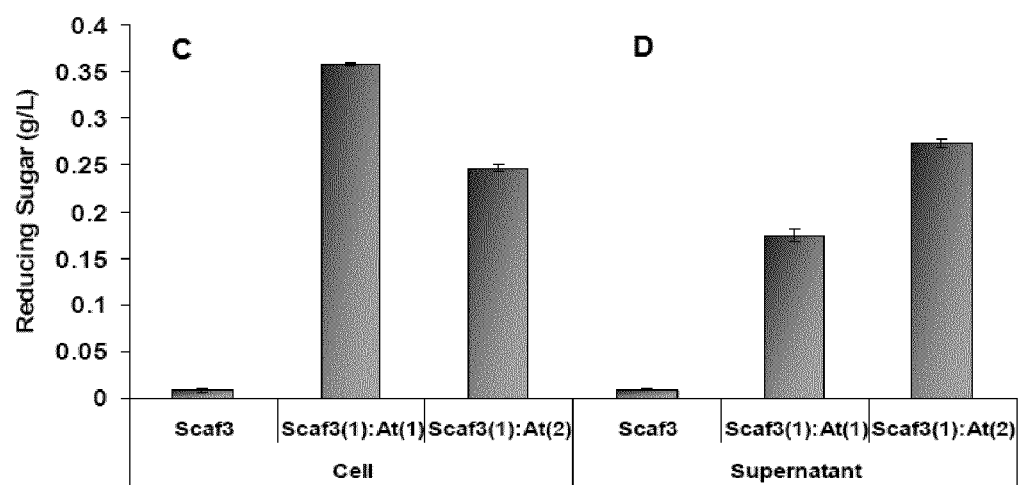
FIGURE 5C-D

SEQUENCE LISTING

<160> NUMBER OF SEQ ID NOS: 8

<210> SEQ ID NO 1
<211> LENGTH: 2052
<212> TYPE: DNA
<213> ORGANISM: Artificial Sequence
<220> FEATURE:
<223> OTHER INFORMATION: Recombinant scaffoldin polypeptide
<220> FEATURE:
<221> NAME/KEY: CDS
<222> LOCATION: (1)..(2052)

<400> SEQUENCE: 1

```
atg ggc gat tct ctt aaa gtt aca gta gga aca gct aat ggt aag cct      48
Met Gly Asp Ser Leu Lys Val Thr Val Gly Thr Ala Asn Gly Lys Pro
1               5                   10                  15 ggc gat aca gta aca gtt cct gtt aca ttt gct gat gta gca aag atg      96
```

```
                                                                                   -continued Gly Asp Thr Val Thr Val Pro Val Thr Phe Ala Asp Val Ala Lys Met
            20                  25                  30 aaa aac gta gga aca tgt aat ttc tat ctt gga tat gat gca agc ctg        144
Lys Asn Val Gly Thr Cys Asn Phe Tyr Leu Gly Tyr Asp Ala Ser Leu
            35                  40                  45 tta gag gta gta tca gta gat gca ggt cca ata gtt aag aat gca gca        192
Leu Glu Val Val Ser Val Asp Ala Gly Pro Ile Val Lys Asn Ala Ala
 50                  55                  60 gtt aac ttc tca agc agt gca agc aac gga aca atc agc ttc ctg ttc        240
Val Asn Phe Ser Ser Ser Ala Ser Asn Gly Thr Ile Ser Phe Leu Phe
 65                  70                  75                  80 ttg gat aac aca att aca gac gaa ttg ata act gca gac ggt gtg ttt        288
Leu Asp Asn Thr Ile Thr Asp Glu Leu Ile Thr Ala Asp Gly Val Phe
                85                  90                  95 gca aat att aag ttc aaa tta aag agt gta acg gct aaa act aca aca        336
Ala Asn Ile Lys Phe Lys Leu Lys Ser Val Thr Ala Lys Thr Thr Thr
            100                 105                 110 cca gta aca ttt aaa gat ggt gga gct ttt ggt gac gga act atg tca        384
Pro Val Thr Phe Lys Asp Gly Gly Ala Phe Gly Asp Gly Thr Met Ser
            115                 120                 125 aag ata gct tca gtt act aag aca aac ggt agt gta acg atc gat ccg        432
Lys Ile Ala Ser Val Thr Lys Thr Asn Gly Ser Val Thr Ile Asp Pro
 130                 135                 140 acc aag gga gca aca cca aca aat aca gct acg ccg aca aaa tca gct        480
Thr Lys Gly Ala Thr Pro Thr Asn Thr Ala Thr Pro Thr Lys Ser Ala
145                 150                 155                 160 acg gct acg ccc acc agg cca tcg gta ccg aca aac aca ccg aca aac        528
Thr Ala Thr Pro Thr Arg Pro Ser Val Pro Thr Asn Thr Pro Thr Asn
                165                 170                 175 aca ccg gca aat aca ccg gta tca ggc aat ttg aag gtt gaa ttc tac        576
Thr Pro Ala Asn Thr Pro Val Ser Gly Asn Leu Lys Val Glu Phe Tyr
            180                 185                 190 aac agc aat cct tca gat act act aac tca atc aat cct cag ttc aag        624
Asn Ser Asn Pro Ser Asp Thr Thr Asn Ser Ile Asn Pro Gln Phe Lys
            195                 200                 205 gtt act aat acc gga agc agt gca att gat ttg tcc aaa ctc aca ttg        672
Val Thr Asn Thr Gly Ser Ser Ala Ile Asp Leu Ser Lys Leu Thr Leu
            210                 215                 220 aga tat tat tat aca gta gac gga cag aaa gat cag acc ttc tgg tgt        720
Arg Tyr Tyr Tyr Thr Val Asp Gly Gln Lys Asp Gln Thr Phe Trp Cys
225                 230                 235                 240 gac cat gct gca ata atc ggc agt aac ggc agc tac aac gga att act        768
Asp His Ala Ala Ile Ile Gly Ser Asn Gly Ser Tyr Asn Gly Ile Thr
                245                 250                 255 tca aat gta aaa gga aca ttt gta aaa atg agt tcc tca aca aat aac        816
Ser Asn Val Lys Gly Thr Phe Val Lys Met Ser Ser Ser Thr Asn Asn
            260                 265                 270 gca gac acc tac ctt gaa ata agc ttt aca ggc gga act ctt gaa ccg        864
Ala Asp Thr Tyr Leu Glu Ile Ser Phe Thr Gly Gly Thr Leu Glu Pro
            275                 280                 285 ggt gca cat gtt cag ata caa ggt aga ttt gca aag aat gac tgg agt        912
Gly Ala His Val Gln Ile Gln Gly Arg Phe Ala Lys Asn Asp Trp Ser
            290                 295                 300 aac tat aca cag tca aat gac tac tca ttc aag tct gct tca cag ttt        960
Asn Tyr Thr Gln Ser Asn Asp Tyr Ser Phe Lys Ser Ala Ser Gln Phe
305                 310                 315                 320 gtt gaa tgg gat cag gta aca gca tac ttg aac ggt gtt ctt gta tgg       1008
Val Glu Trp Asp Gln Val Thr Ala Tyr Leu Asn Gly Val Leu Val Trp
                325                 330                 335
```

```
ggt aaa gaa ccc ggt ggc agt gta gta cca tca aca cag cct gta aca      1056
Gly Lys Glu Pro Gly Gly Ser Val Val Pro Ser Thr Gln Pro Val Thr
            340             345                 350 aca cca cct gca aca aca aaa cca cct gca aca aca aaa cca cct gca      1104
Thr Pro Pro Ala Thr Thr Lys Pro Pro Ala Thr Thr Lys Pro Pro Ala
        355                 360                 365 aca aca ata ccg ccg tca gat gat ccg aat gca ata aag att aag gtg      1152
Thr Thr Ile Pro Pro Ser Asp Asp Pro Asn Ala Ile Lys Ile Lys Val
    370                 375                 380 gac aca gta aat gca aaa ccg gga gac aca gta aat ata cct gta aga      1200
Asp Thr Val Asn Ala Lys Pro Gly Asp Thr Val Asn Ile Pro Val Arg
385                 390                 395                 400 ttc agt ggt ata cca tcc aag gga ata gca aac tgt gac ttt gta tac      1248
Phe Ser Gly Ile Pro Ser Lys Gly Ile Ala Asn Cys Asp Phe Val Tyr
                405                 410                 415 agc tat gac ccg aat gta ctt gag ata ata gag ata aaa ccg gga gaa      1296
Ser Tyr Asp Pro Asn Val Leu Glu Ile Ile Glu Ile Lys Pro Gly Glu
            420                 425                 430 ttg ata gtt gac ccg aat cct gac aag agc ttt gat act gca gta tat      1344
Leu Ile Val Asp Pro Asn Pro Asp Lys Ser Phe Asp Thr Ala Val Tyr
        435                 440                 445 cct gac aga aag ata ata gta ttc ctg ttt gca gaa gac agc gga aca      1392
Pro Asp Arg Lys Ile Ile Val Phe Leu Phe Ala Glu Asp Ser Gly Thr
450                 455                 460 gga gcg tat gca ata act aaa gac gga gta ttt gct acg ata gta gcg      1440
Gly Ala Tyr Ala Ile Thr Lys Asp Gly Val Phe Ala Thr Ile Val Ala
465                 470                 475                 480 aaa gta aaa tcc gga gca cct aac gga ctc agt gta atc aaa ttt gta      1488
Lys Val Lys Ser Gly Ala Pro Asn Gly Leu Ser Val Ile Lys Phe Val
                485                 490                 495 gaa gta ggc gga ttt gcg aac aat gac ctt gta gaa cag agg aca cag      1536
Glu Val Gly Gly Phe Ala Asn Asn Asp Leu Val Glu Gln Arg Thr Gln
            500                 505                 510 ttc ttt gac ggt gga gta aat gtt gga gat ata gga tcc gcc ggt ggt      1584
Phe Phe Asp Gly Gly Val Asn Val Gly Asp Ile Gly Ser Ala Gly Gly
        515                 520                 525 tta tcc gct gtg cag cct aat gtt agt tta ggc gaa gta ctg gat gtt      1632
Leu Ser Ala Val Gln Pro Asn Val Ser Leu Gly Glu Val Leu Asp Val
530                 535                 540 tct gct aac aga acc gct gct gac gga aca gtt gaa tgg ctt atc cca      1680
Ser Ala Asn Arg Thr Ala Ala Asp Gly Thr Val Glu Trp Leu Ile Pro
545                 550                 555                 560 aca gta act gca gct cca ggc cag acg gtc act atg ccc gta gta gtc      1728
Thr Val Thr Ala Ala Pro Gly Gln Thr Val Thr Met Pro Val Val Val
                565                 570                 575 aag agt tca agt ctt gca gtt gct ggt gcg cag ttc aag atc cag gcg      1776
Lys Ser Ser Ser Leu Ala Val Ala Gly Ala Gln Phe Lys Ile Gln Ala
            580                 585                 590 gcg aca ggc gta agt tat tcg tcc aag acg gac ggt gac gct tac ggt      1824
Ala Thr Gly Val Ser Tyr Ser Ser Lys Thr Asp Gly Asp Ala Tyr Gly
        595                 600                 605 tca ggc att gtg tac aat aat agt aag tat gct ttt gga cag ggt gca      1872
Ser Gly Ile Val Tyr Asn Asn Ser Lys Tyr Ala Phe Gly Gln Gly Ala
610                 615                 620 ggt aga gga ata gtt gca gct gat gat tcg gtt gtg ctt act ctt gca      1920
Gly Arg Gly Ile Val Ala Ala Asp Asp Ser Val Val Leu Thr Leu Ala
625                 630                 635                 640 tat aca gtt ccc gct gat tgt gct gaa ggt aca tat gat gtc aag tgg      1968
Tyr Thr Val Pro Ala Asp Cys Ala Glu Gly Thr Tyr Asp Val Lys Trp
                645                 650                 655
```

```
tct gat gcg ttt gta agt gat aca gac gga cag aat atc aca agt aag    2016
Ser Asp Ala Phe Val Ser Asp Thr Asp Gly Gln Asn Ile Thr Ser Lys
            660                 665                 670 gtt act ctt act gat ggc gct atc att gtt aag tag                    2052
Val Thr Leu Thr Asp Gly Ala Ile Ile Val Lys
    675                 680
```

<210> SEQ ID NO 2
<211> LENGTH: 683
<212> TYPE: PRT
<213> ORGANISM: Artificial Sequence
<220> FEATURE:
<223> OTHER INFORMATION: Synthetic Construct

<400> SEQUENCE: 2

```
Met Gly Asp Ser Leu Lys Val Thr Val Gly Thr Ala Asn Gly Lys Pro
1               5                   10                  15

Gly Asp Thr Val Thr Val Pro Val Thr Phe Ala Asp Val Ala Lys Met
            20                  25                  30

Lys Asn Val Gly Thr Cys Asn Phe Tyr Leu Gly Tyr Asp Ala Ser Leu
        35                  40                  45

Leu Glu Val Val Ser Val Asp Ala Gly Pro Ile Val Lys Asn Ala Ala
    50                  55                  60

Val Asn Phe Ser Ser Ser Ala Ser Asn Gly Thr Ile Ser Phe Leu Phe
65                  70                  75                  80

Leu Asp Asn Thr Ile Thr Asp Glu Leu Ile Thr Ala Asp Gly Val Phe
                85                  90                  95

Ala Asn Ile Lys Phe Lys Leu Lys Ser Val Thr Ala Lys Thr Thr Thr
            100                 105                 110

Pro Val Thr Phe Lys Asp Gly Gly Ala Phe Gly Asp Gly Thr Met Ser
        115                 120                 125

Lys Ile Ala Ser Val Thr Lys Thr Asn Gly Ser Val Thr Ile Asp Pro
    130                 135                 140

Thr Lys Gly Ala Thr Pro Thr Asn Thr Ala Thr Pro Thr Lys Ser Ala
145                 150                 155                 160

Thr Ala Thr Pro Thr Arg Pro Ser Val Pro Thr Asn Thr Pro Thr Asn
                165                 170                 175

Thr Pro Ala Asn Thr Pro Val Ser Gly Asn Leu Lys Val Glu Phe Tyr
            180                 185                 190

Asn Ser Asn Pro Ser Asp Thr Thr Asn Ser Ile Asn Pro Gln Phe Lys
        195                 200                 205

Val Thr Asn Thr Gly Ser Ser Ala Ile Asp Leu Ser Lys Leu Thr Leu
    210                 215                 220

Arg Tyr Tyr Tyr Thr Val Asp Gly Gln Lys Asp Gln Thr Phe Trp Cys
225                 230                 235                 240

Asp His Ala Ala Ile Ile Gly Ser Asn Gly Ser Tyr Asn Gly Ile Thr
                245                 250                 255

Ser Asn Val Lys Gly Thr Phe Val Lys Met Ser Ser Ser Thr Asn Asn
            260                 265                 270

Ala Asp Thr Tyr Leu Glu Ile Ser Phe Thr Gly Gly Thr Leu Glu Pro
        275                 280                 285

Gly Ala His Val Gln Ile Gln Gly Arg Phe Ala Lys Asn Asp Trp Ser
    290                 295                 300

Asn Tyr Thr Gln Ser Asn Asp Tyr Ser Phe Lys Ser Ala Ser Gln Phe
305                 310                 315                 320
```

```
Val Glu Trp Asp Gln Val Thr Ala Tyr Leu Asn Gly Val Leu Val Trp
            325                 330                 335

Gly Lys Glu Pro Gly Gly Ser Val Val Pro Ser Thr Gln Pro Val Thr
        340                 345                 350

Thr Pro Pro Ala Thr Thr Lys Pro Pro Ala Thr Thr Lys Pro Pro Ala
    355                 360                 365

Thr Thr Ile Pro Pro Ser Asp Asp Pro Asn Ala Ile Lys Ile Lys Val
370                 375                 380

Asp Thr Val Asn Ala Lys Pro Gly Asp Thr Val Asn Ile Pro Val Arg
385                 390                 395                 400

Phe Ser Gly Ile Pro Ser Lys Gly Ile Ala Asn Cys Asp Phe Val Tyr
                405                 410                 415

Ser Tyr Asp Pro Asn Val Leu Glu Ile Glu Ile Lys Pro Gly Glu
            420                 425                 430

Leu Ile Val Asp Pro Asn Pro Asp Lys Ser Phe Asp Thr Ala Val Tyr
        435                 440                 445

Pro Asp Arg Lys Ile Ile Val Phe Leu Phe Ala Glu Asp Ser Gly Thr
    450                 455                 460

Gly Ala Tyr Ala Ile Thr Lys Asp Gly Val Phe Ala Thr Ile Val Ala
465                 470                 475                 480

Lys Val Lys Ser Gly Ala Pro Asn Gly Leu Ser Val Ile Lys Phe Val
                485                 490                 495

Glu Val Gly Gly Phe Ala Asn Asn Asp Leu Val Glu Gln Arg Thr Gln
            500                 505                 510

Phe Phe Asp Gly Gly Val Asn Val Gly Asp Ile Gly Ser Ala Gly Gly
        515                 520                 525

Leu Ser Ala Val Gln Pro Asn Val Ser Leu Gly Glu Val Leu Asp Val
530                 535                 540

Ser Ala Asn Arg Thr Ala Ala Asp Gly Thr Val Glu Trp Leu Ile Pro
545                 550                 555                 560

Thr Val Thr Ala Ala Pro Gly Gln Thr Val Thr Met Pro Val Val Val
                565                 570                 575

Lys Ser Ser Ser Leu Ala Val Ala Gly Ala Gln Phe Lys Ile Gln Ala
            580                 585                 590

Ala Thr Gly Val Ser Tyr Ser Ser Lys Thr Asp Gly Asp Ala Tyr Gly
        595                 600                 605

Ser Gly Ile Val Tyr Asn Asn Ser Lys Tyr Ala Phe Gly Gln Gly Ala
610                 615                 620

Gly Arg Gly Ile Val Ala Ala Asp Asp Ser Val Val Leu Thr Leu Ala
625                 630                 635                 640

Tyr Thr Val Pro Ala Asp Cys Ala Glu Gly Thr Tyr Asp Val Lys Trp
                645                 650                 655

Ser Asp Ala Phe Val Ser Asp Thr Asp Gly Gln Asn Ile Thr Ser Lys
            660                 665                 670

Val Thr Leu Thr Asp Gly Ala Ile Ile Val Lys
        675                 680

<210> SEQ ID NO 3
<211> LENGTH: 2580
<212> TYPE: DNA
<213> ORGANISM: C. cellulolytica
<220> FEATURE:
<221> NAME/KEY: CDS
<222> LOCATION: (1)..(2580)

<400> SEQUENCE: 3
```

-continued

```
atg ctt gtt ggg gca gga gat ttg att cga aac cat acc ttt gac aac      48
Met Leu Val Gly Ala Gly Asp Leu Ile Arg Asn His Thr Phe Asp Asn
1               5                  10                  15 aga gta ggt ctt cca tgg cac gtg gtt gaa tca tac cct gca aag gca      96
Arg Val Gly Leu Pro Trp His Val Val Glu Ser Tyr Pro Ala Lys Ala
            20                  25                  30 agt ttt gaa att aca tct gat ggt aag tac aag ata act gct caa aag     144
Ser Phe Glu Ile Thr Ser Asp Gly Lys Tyr Lys Ile Thr Ala Gln Lys
        35                  40                  45 atc ggt gag gca gga aaa ggt gaa aga tgg gat ata caa ttc cgt cac     192
Ile Gly Glu Ala Gly Lys Gly Glu Arg Trp Asp Ile Gln Phe Arg His
    50                  55                  60 aga gga ctc gca ttg caa caa ggt cat act tat aca gta aag ttt act     240
Arg Gly Leu Ala Leu Gln Gln Gly His Thr Tyr Thr Val Lys Phe Thr
65                  70                  75                  80 gtt act gct agc aga gct tgt aaa att tat cct aaa ata ggt gac cag     288
Val Thr Ala Ser Arg Ala Cys Lys Ile Tyr Pro Lys Ile Gly Asp Gln
                85                  90                  95 ggt gat cca tat gat gaa tac tgg aat atg aat caa caa tgg aat ttc     336
Gly Asp Pro Tyr Asp Glu Tyr Trp Asn Met Asn Gln Gln Trp Asn Phe
            100                 105                 110 ctg gaa tta cag gct aat act cca aaa act gta act cag aca ttt aca     384
Leu Glu Leu Gln Ala Asn Thr Pro Lys Thr Val Thr Gln Thr Phe Thr
        115                 120                 125 cag act aag gga gat aag aag aac gtt gaa ttt gct ttt cac ctt gct     432
Gln Thr Lys Gly Asp Lys Lys Asn Val Glu Phe Ala Phe His Leu Ala
    130                 135                 140 ccc gat aaa act aca tct gag gca cag aat cca gca agt ttc caa cct     480
Pro Asp Lys Thr Thr Ser Glu Ala Gln Asn Pro Ala Ser Phe Gln Pro
145                 150                 155                 160 ata aca tat act ttt gat gaa att tat att cag gac cct caa ttt gca     528
Ile Thr Tyr Thr Phe Asp Glu Ile Tyr Ile Gln Asp Pro Gln Phe Ala
                165                 170                 175 gga tat act gaa gat cca cct gaa cct act aat gtt gta cgt ttg aat     576
Gly Tyr Thr Glu Asp Pro Pro Glu Pro Thr Asn Val Val Arg Leu Asn
            180                 185                 190 cag gta ggt ttc tat cct aat gct gat aag att gca aca gta gca aca     624
Gln Val Gly Phe Tyr Pro Asn Ala Asp Lys Ile Ala Thr Val Ala Thr
        195                 200                 205 agt tca aca act cca att aac tgg cag ttg gtt aat agt act gga gca     672
Ser Ser Thr Thr Pro Ile Asn Trp Gln Leu Val Asn Ser Thr Gly Ala
    210                 215                 220 gct gtt tta aca ggt aaa tca act gtt aaa ggt gcc gac cgt gca tca     720
Ala Val Leu Thr Gly Lys Ser Thr Val Lys Gly Ala Asp Arg Ala Ser
225                 230                 235                 240 ggt gat aat gtc cat atc att gat ttc tct agt tac aca aca cct ggt     768
Gly Asp Asn Val His Ile Ile Asp Phe Ser Ser Tyr Thr Thr Pro Gly
                245                 250                 255 acc gac tat aag ata gta aca gat gta tca gta aca aaa gcc gga gac     816
Thr Asp Tyr Lys Ile Val Thr Asp Val Ser Val Thr Lys Ala Gly Asp
            260                 265                 270 aat gaa agt atg aag ttc aat att gga gat gac ctt ttt act caa atg     864
Asn Glu Ser Met Lys Phe Asn Ile Gly Asp Asp Leu Phe Thr Gln Met
        275                 280                 285 aaa tac gat tca atg aag tat ttc tat cac aac aga agt gct att cca     912
Lys Tyr Asp Ser Met Lys Tyr Phe Tyr His Asn Arg Ser Ala Ile Pro
    290                 295                 300 ata caa atg cca tac tgt gat caa tca caa tgg gca cgt cct gca gga     960
Ile Gln Met Pro Tyr Cys Asp Gln Ser Gln Trp Ala Arg Pro Ala Gly
```

```
                305                  310                  315                  320
cac aca act gat ata ctt gct cca gat cca aca aag gat tac aag gct   1008
His Thr Thr Asp Ile Leu Ala Pro Asp Pro Thr Lys Asp Tyr Lys Ala
                        325                  330                  335 aac tac aca ctt gac gtt aca ggt ggt tgg tat gat gcc ggt gac cat   1056
Asn Tyr Thr Leu Asp Val Thr Gly Gly Trp Tyr Asp Ala Gly Asp His
                340                  345                  350 ggt aag tat gtt gtt aat ggt ggt att gca acc tgg acc gta atg aat   1104
Gly Lys Tyr Val Val Asn Gly Gly Ile Ala Thr Trp Thr Val Met Asn
            355                  360                  365 gca tat gag cgt gca cta cac atg ggt gga gac act tca gtt gct cca   1152
Ala Tyr Glu Arg Ala Leu His Met Gly Gly Asp Thr Ser Val Ala Pro
        370                  375                  380 ttt aaa gac ggt tct tta gca ata cca gaa gcg gaa gtc tat cct gac   1200
Phe Lys Asp Gly Ser Leu Ala Ile Pro Glu Ala Glu Val Tyr Pro Asp
385                  390                  395                  400 ata ctg gac gaa gct cgt tac cag ctc att aac atg aaa aca tta tta   1248
Ile Leu Asp Glu Ala Arg Tyr Gln Leu Ile Asn Met Lys Thr Leu Leu
                    405                  410                  415 aat agt cag gtt cca gca gga aag tat gcg ggt atg gct cac cac aaa   1296
Asn Ser Gln Val Pro Ala Gly Lys Tyr Ala Gly Met Ala His His Lys
                420                  425                  430 gct cat gac gaa cgt tgg aca gct ctt gct gta cgt ccc gac cag gat   1344
Ala His Asp Glu Arg Trp Thr Ala Leu Ala Val Arg Pro Asp Gln Asp
            435                  440                  445 aca atg aaa cgt tgg ttg cag cct cca agt aca gca gct aca tta aat   1392
Thr Met Lys Arg Trp Leu Gln Pro Pro Ser Thr Ala Ala Thr Leu Asn
        450                  455                  460 ctg gct gct att gct gca caa agt tca cgt ctt tgg aaa cag ttt gat   1440
Leu Ala Ala Ile Ala Ala Gln Ser Ser Arg Leu Trp Lys Gln Phe Asp
465                  470                  475                  480 tct gct ttc gca act aag tgt tta act gca gca gaa act gct agg gat   1488
Ser Ala Phe Ala Thr Lys Cys Leu Thr Ala Ala Glu Thr Ala Arg Asp
                    485                  490                  495 gca gct gta gct cat cca gaa ata tat gca act atg gaa cag ggt gcc   1536
Ala Ala Val Ala His Pro Glu Ile Tyr Ala Thr Met Glu Gln Gly Ala
                500                  505                  510 ggt ggt gga gca tac gga gac aac tat gtt ctt gat gat ttc tac tgg   1584
Gly Gly Gly Ala Tyr Gly Asp Asn Tyr Val Leu Asp Asp Phe Tyr Trp
            515                  520                  525 gca gca tgt gaa ttg tat gca act aca ggc agt gac aag tat ttg aac   1632
Ala Ala Cys Glu Leu Tyr Ala Thr Thr Gly Ser Asp Lys Tyr Leu Asn
        530                  535                  540 tac ata aag agc tca aag cat tat ctc gaa atg cct aca gaa tta aca   1680
Tyr Ile Lys Ser Ser Lys His Tyr Leu Glu Met Pro Thr Glu Leu Thr
545                  550                  555                  560 ggc ggt gag aat act gga att aca ggg gct ttt gac tgg ggt tgt aca   1728
Gly Gly Glu Asn Thr Gly Ile Thr Gly Ala Phe Asp Trp Gly Cys Thr
                    565                  570                  575 gca ggt atg gga aca ata aca ctt gca ctt gta cct aca aag ctt ccg   1776
Ala Gly Met Gly Thr Ile Thr Leu Ala Leu Val Pro Thr Lys Leu Pro
                580                  585                  590 gca gca gat gtt gct aca gct aaa gct aat att caa gct gca gct gat   1824
Ala Ala Asp Val Ala Thr Ala Lys Ala Asn Ile Gln Ala Ala Ala Asp
            595                  600                  605 aag ttc ata tca att tca aaa gca caa ggc tat ggt gta cca cta gaa   1872
Lys Phe Ile Ser Ile Ser Lys Ala Gln Gly Tyr Gly Val Pro Leu Glu
        610                  615                  620 gaa aaa gta att tca tct cct ttt gat gca tct gtt gtt aaa ggt ttc   1920
```

|  |  |
|---|---|
| Glu Lys Val Ile Ser Ser Pro Phe Asp Ala Ser Val Val Lys Gly Phe<br>625                      630                      635                      640 |  |
| caa tgg gga tca aac tca ttc gtt att aat gaa gca ata gtt atg tca<br>Gln Trp Gly Ser Asn Ser Phe Val Ile Asn Glu Ala Ile Val Met Ser<br>                    645                      650                      655 | 1968 |
| tat gct tat gaa ttc agc gat gtt aat ggc aca aag aat aat aaa tat<br>Tyr Ala Tyr Glu Phe Ser Asp Val Asn Gly Thr Lys Asn Asn Lys Tyr<br>660                      665                      670 | 2016 |
| att aat ggt gct tta aca gca atg gat tac ctc ctc gga cgt aac cca<br>Ile Asn Gly Ala Leu Thr Ala Met Asp Tyr Leu Leu Gly Arg Asn Pro<br>                675                      680                      685 | 2064 |
| aat att caa agc tat ata act ggt tat ggt gac aac cca ctt gaa aat<br>Asn Ile Gln Ser Tyr Ile Thr Gly Tyr Gly Asp Asn Pro Leu Glu Asn<br>690                      695                      700 | 2112 |
| cct cat cac cgt ttc tgg gca tac cag gca gac aac aca ttc cca aaa<br>Pro His His Arg Phe Trp Ala Tyr Gln Ala Asp Asn Thr Phe Pro Lys<br>705                      710                      715                      720 | 2160 |
| cca cct ccg gga tgt ctg tca gga gga cct aac tcc ggc ttg cag gat<br>Pro Pro Pro Gly Cys Leu Ser Gly Gly Pro Asn Ser Gly Leu Gln Asp<br>                725                      730                      735 | 2208 |
| cct tgg gtt aag ggt tca ggc tgg cag cca ggt gaa aga cct gct gaa<br>Pro Trp Val Lys Gly Ser Gly Trp Gln Pro Gly Glu Arg Pro Ala Glu<br>                    740                      745                      750 | 2256 |
| aaa tgc ttc atg gac aat att gaa tct tgg tca aca aac gaa ata acc<br>Lys Cys Phe Met Asp Asn Ile Glu Ser Trp Ser Thr Asn Glu Ile Thr<br>755                      760                      765 | 2304 |
| atc aac tgg aat gct cct ctt gta tgg ata tca gct tac ctt gat gaa<br>Ile Asn Trp Asn Ala Pro Leu Val Trp Ile Ser Ala Tyr Leu Asp Glu<br>770                      775                      780 | 2352 |
| aag ggg cca gag att ggt ggg tca gtg act cct cca act aat tta gga<br>Lys Gly Pro Glu Ile Gly Gly Ser Val Thr Pro Pro Thr Asn Leu Gly<br>785                      790                      795                      800 | 2400 |
| gat gtt aac ggc gat gga aac aag gat gca ttg gac ttc gct gca ttg<br>Asp Val Asn Gly Asp Gly Asn Lys Asp Ala Leu Asp Phe Ala Ala Leu<br>                    805                      810                      815 | 2448 |
| aag aaa gcc ttg tta agc cag gat act tct act ata aat gtt gct aat<br>Lys Lys Ala Leu Leu Ser Gln Asp Thr Ser Thr Ile Asn Val Ala Asn<br>820                      825                      830 | 2496 |
| gct gat ata aac aaa gat ggt tct att gat gca gtt gac ttt gca tta<br>Ala Asp Ile Asn Lys Asp Gly Ser Ile Asp Ala Val Asp Phe Ala Leu<br>                835                      840                      845 | 2544 |
| ctc aaa tca ttc ttg tta gga aaa atc aca cag tga<br>Leu Lys Ser Phe Leu Leu Gly Lys Ile Thr Gln<br>850                      855 | 2580 |

<210> SEQ ID NO 4
<211> LENGTH: 859
<212> TYPE: PRT
<213> ORGANISM: C. cellulolytica

<400> SEQUENCE: 4

Met Leu Val Gly Ala Gly Asp Leu Ile Arg Asn His Thr Phe Asp Asn
1                 5                     10                    15

Arg Val Gly Leu Pro Trp His Val Val Glu Ser Tyr Pro Ala Lys Ala
                 20                     25                     30

Ser Phe Glu Ile Thr Ser Asp Gly Lys Tyr Lys Ile Thr Ala Gln Lys
            35                     40                    45

Ile Gly Glu Ala Gly Lys Gly Glu Arg Trp Asp Ile Gln Phe Arg His
50                      55                     60

-continued

```
Arg Gly Leu Ala Leu Gln Gln Gly His Thr Tyr Thr Val Lys Phe Thr
 65                  70                  75                  80

Val Thr Ala Ser Arg Ala Cys Lys Ile Tyr Pro Lys Ile Gly Asp Gln
                 85                  90                  95

Gly Asp Pro Tyr Asp Glu Tyr Trp Asn Met Asn Gln Gln Trp Asn Phe
            100                 105                 110

Leu Glu Leu Gln Ala Asn Thr Pro Lys Thr Val Thr Gln Thr Phe Thr
        115                 120                 125

Gln Thr Lys Gly Asp Lys Lys Asn Val Glu Phe Ala Phe His Leu Ala
130                 135                 140

Pro Asp Lys Thr Thr Ser Glu Ala Gln Asn Pro Ala Ser Phe Gln Pro
145                 150                 155                 160

Ile Thr Tyr Thr Phe Asp Glu Ile Tyr Ile Gln Asp Pro Gln Phe Ala
                165                 170                 175

Gly Tyr Thr Glu Asp Pro Pro Glu Pro Thr Asn Val Val Arg Leu Asn
            180                 185                 190

Gln Val Gly Phe Tyr Pro Asn Ala Asp Lys Ile Ala Thr Val Ala Thr
        195                 200                 205

Ser Ser Thr Thr Pro Ile Asn Trp Gln Leu Val Asn Ser Thr Gly Ala
210                 215                 220

Ala Val Leu Thr Gly Lys Ser Thr Val Lys Gly Ala Asp Arg Ala Ser
225                 230                 235                 240

Gly Asp Asn Val His Ile Ile Asp Phe Ser Tyr Thr Thr Pro Gly
                245                 250                 255

Thr Asp Tyr Lys Ile Val Thr Val Ser Val Thr Lys Ala Gly Asp
            260                 265                 270

Asn Glu Ser Met Lys Phe Asn Ile Gly Asp Asp Leu Phe Thr Gln Met
        275                 280                 285

Lys Tyr Asp Ser Met Lys Tyr Phe Tyr His Asn Arg Ser Ala Ile Pro
290                 295                 300

Ile Gln Met Pro Tyr Cys Asp Gln Ser Gln Trp Ala Arg Pro Ala Gly
305                 310                 315                 320

His Thr Thr Asp Ile Leu Ala Pro Asp Pro Thr Lys Asp Tyr Lys Ala
                325                 330                 335

Asn Tyr Thr Leu Asp Val Thr Gly Gly Trp Tyr Asp Ala Gly Asp His
            340                 345                 350

Gly Lys Tyr Val Val Asn Gly Gly Ile Ala Thr Trp Thr Val Met Asn
        355                 360                 365

Ala Tyr Glu Arg Ala Leu His Met Gly Gly Asp Thr Ser Val Ala Pro
370                 375                 380

Phe Lys Asp Gly Ser Leu Ala Ile Pro Glu Ala Glu Val Tyr Pro Asp
385                 390                 395                 400

Ile Leu Asp Glu Ala Arg Tyr Gln Leu Ile Asn Met Lys Thr Leu Leu
                405                 410                 415

Asn Ser Gln Val Pro Ala Gly Lys Tyr Ala Gly Met Ala His His Lys
            420                 425                 430

Ala His Asp Glu Arg Trp Thr Ala Leu Ala Val Arg Pro Asp Gln Asp
        435                 440                 445

Thr Met Lys Arg Trp Leu Gln Pro Ser Thr Ala Ala Thr Leu Asn
450                 455                 460

Leu Ala Ala Ile Ala Ala Gln Ser Ser Arg Leu Trp Lys Gln Phe Asp
465                 470                 475                 480

Ser Ala Phe Ala Thr Lys Cys Leu Thr Ala Ala Glu Thr Ala Arg Asp
```

```
            485                 490                 495
Ala Ala Val Ala His Pro Glu Ile Tyr Ala Thr Met Glu Gln Gly Ala
            500                 505                 510
Gly Gly Gly Ala Tyr Gly Asp Asn Tyr Val Leu Asp Asp Phe Tyr Trp
            515                 520                 525
Ala Ala Cys Glu Leu Tyr Ala Thr Thr Gly Ser Asp Lys Tyr Leu Asn
            530                 535                 540
Tyr Ile Lys Ser Ser Lys His Tyr Leu Glu Met Pro Thr Glu Leu Thr
545                 550                 555                 560
Gly Gly Glu Asn Thr Gly Ile Thr Gly Ala Phe Asp Trp Gly Cys Thr
            565                 570                 575
Ala Gly Met Gly Thr Ile Thr Leu Ala Leu Val Pro Thr Lys Leu Pro
            580                 585                 590
Ala Ala Asp Val Ala Thr Ala Lys Ala Asn Ile Gln Ala Ala Ala Asp
            595                 600                 605
Lys Phe Ile Ser Ile Ser Lys Ala Gln Gly Tyr Gly Val Pro Leu Glu
            610                 615                 620
Glu Lys Val Ile Ser Ser Pro Phe Asp Ala Ser Val Val Lys Gly Phe
625                 630                 635                 640
Gln Trp Gly Ser Asn Ser Phe Val Ile Asn Glu Ala Ile Val Met Ser
            645                 650                 655
Tyr Ala Tyr Glu Phe Ser Asp Val Asn Gly Thr Lys Asn Asn Lys Tyr
            660                 665                 670
Ile Asn Gly Ala Leu Thr Ala Met Asp Tyr Leu Leu Gly Arg Asn Pro
            675                 680                 685
Asn Ile Gln Ser Tyr Ile Thr Gly Tyr Gly Asp Asn Pro Leu Glu Asn
            690                 695                 700
Pro His His Arg Phe Trp Ala Tyr Gln Ala Asp Asn Thr Phe Pro Lys
705                 710                 715                 720
Pro Pro Pro Gly Cys Leu Ser Gly Gly Pro Asn Ser Gly Leu Gln Asp
            725                 730                 735
Pro Trp Val Lys Gly Ser Gly Trp Gln Pro Gly Glu Arg Pro Ala Glu
            740                 745                 750
Lys Cys Phe Met Asp Asn Ile Glu Ser Trp Ser Thr Asn Glu Ile Thr
            755                 760                 765
Ile Asn Trp Asn Ala Pro Leu Val Trp Ile Ser Ala Tyr Leu Asp Glu
            770                 775                 780
Lys Gly Pro Glu Ile Gly Gly Ser Val Thr Pro Thr Asn Leu Gly
785                 790                 795                 800
Asp Val Asn Gly Asp Gly Asn Lys Asp Ala Leu Asp Phe Ala Ala Leu
            805                 810                 815
Lys Lys Ala Leu Leu Ser Gln Asp Thr Ser Thr Ile Asn Val Ala Asn
            820                 825                 830
Ala Asp Ile Asn Lys Asp Gly Ser Ile Asp Ala Val Asp Phe Ala Leu
            835                 840                 845
Leu Lys Ser Phe Leu Leu Gly Lys Ile Thr Gln
850                 855

<210> SEQ ID NO 5
<211> LENGTH: 2118
<212> TYPE: DNA
<213> ORGANISM: Artificial Sequence
<220> FEATURE:
<223> OTHER INFORMATION: Fusion consruct enzyme-dockerin
<220> FEATURE:
```

```
<221> NAME/KEY: CDS
<222> LOCATION: (1)..(2118)

<400> SEQUENCE: 5 atg gga aca tat aac tat gga gaa gca tta cag aaa tca ata atg ttc      48
Met Gly Thr Tyr Asn Tyr Gly Glu Ala Leu Gln Lys Ser Ile Met Phe
1               5                  10                  15 tat gaa ttc cag cgt tcg gga gat ctt ccg gct gat aaa cgt gac aac      96
Tyr Glu Phe Gln Arg Ser Gly Asp Leu Pro Ala Asp Lys Arg Asp Asn
            20                  25                  30 tgg aga gac gat tcc ggt atg aaa gac ggt tct gat gta gga gtt gat     144
Trp Arg Asp Asp Ser Gly Met Lys Asp Gly Ser Asp Val Gly Val Asp
        35                  40                  45 ctt aca gga gga tgg tac gat gca ggt gac cat gtg aaa ttt aat cta     192
Leu Thr Gly Gly Trp Tyr Asp Ala Gly Asp His Val Lys Phe Asn Leu
    50                  55                  60 cct atg tca tat aca tct gca atg ctt gca tgg tcc tta tat gag gat     240
Pro Met Ser Tyr Thr Ser Ala Met Leu Ala Trp Ser Leu Tyr Glu Asp
65                  70                  75                  80 aag gat gct tat gat aag agc ggt cag aca aaa tat ata atg gac ggt     288
Lys Asp Ala Tyr Asp Lys Ser Gly Gln Thr Lys Tyr Ile Met Asp Gly
                85                  90                  95 ata aaa tgg gct aat gat tat ttt att aaa tgt aat ccg aca ccc ggt     336
Ile Lys Trp Ala Asn Asp Tyr Phe Ile Lys Cys Asn Pro Thr Pro Gly
            100                 105                 110 gta tat tat tac caa gta gga gac ggc gga aag gac cac tct tgg tgg     384
Val Tyr Tyr Tyr Gln Val Gly Asp Gly Gly Lys Asp His Ser Trp Trp
        115                 120                 125 ggc cct gcg gaa gta atg cag atg gaa aga ccg tct ttt aag gtt gac     432
Gly Pro Ala Glu Val Met Gln Met Glu Arg Pro Ser Phe Lys Val Asp
    130                 135                 140 gct tct aag ccc ggt tct gca gta tgt gct tcc act gca gct tct ctg     480
Ala Ser Lys Pro Gly Ser Ala Val Cys Ala Ser Thr Ala Ala Ser Leu
145                 150                 155                 160 gca tct gca gca gta gtc ttt aaa tcc agt gat cct act tat gca gaa     528
Ala Ser Ala Ala Val Val Phe Lys Ser Ser Asp Pro Thr Tyr Ala Glu
                165                 170                 175 aag tgc ata agc cat gca aag aac ctg ttt gat atg gct gac aaa gca     576
Lys Cys Ile Ser His Ala Lys Asn Leu Phe Asp Met Ala Asp Lys Ala
            180                 185                 190 aag agt gat gct ggt tat act gcg gct tca ggc tac tac agc tca agc     624
Lys Ser Asp Ala Gly Tyr Thr Ala Ala Ser Gly Tyr Tyr Ser Ser Ser
        195                 200                 205 tca ttt tac gat gat ctc tca tgg gct gca gta tgg tta tat ctt gct     672
Ser Phe Tyr Asp Asp Leu Ser Trp Ala Ala Val Trp Leu Tyr Leu Ala
    210                 215                 220 aca aat gac agt aca tat tta gac aaa gca gaa tcc tat gta ccg aat     720
Thr Asn Asp Ser Thr Tyr Leu Asp Lys Ala Glu Ser Tyr Val Pro Asn
225                 230                 235                 240 tgg ggt aaa gaa cag cag aca gat att atc gcc tac aag tgg gga cag     768
Trp Gly Lys Glu Gln Gln Thr Asp Ile Ile Ala Tyr Lys Trp Gly Gln
                245                 250                 255 tgc tgg gat gat gtt cat tat ggt gct gag ctt ctt ctt gca aag ctt     816
Cys Trp Asp Asp Val His Tyr Gly Ala Glu Leu Leu Leu Ala Lys Leu
            260                 265                 270 aca aac aaa caa ttg tat aag gat agt ata gaa atg aac ctt gac ttc     864
Thr Asn Lys Gln Leu Tyr Lys Asp Ser Ile Glu Met Asn Leu Asp Phe
        275                 280                 285 tgg aca act ggt gtt aac gga aca cgt gtt tct tac acg cca aag ggt     912
Trp Thr Thr Gly Val Asn Gly Thr Arg Val Ser Tyr Thr Pro Lys Gly
```

-continued

```
                    290                 295                 300
ttg gcg tgg cta ttc caa tgg ggt tca tta aga cat gct aca act cag      960
Leu Ala Trp Leu Phe Gln Trp Gly Ser Leu Arg His Ala Thr Thr Gln
305                 310                 315                 320 gct ttt tta gcc ggt gtt tat gca gag tgg gaa ggc tgt acg cca tcc     1008
Ala Phe Leu Ala Gly Val Tyr Ala Glu Trp Glu Gly Cys Thr Pro Ser
                325                 330                 335 aaa gta tct gta tat aag gat ttc ctc aag agt caa att gat tat gca     1056
Lys Val Ser Val Tyr Lys Asp Phe Leu Lys Ser Gln Ile Asp Tyr Ala
            340                 345                 350 ctt ggc agt acc gga aga agt ttt gtt gtc gga tat gga gta aat cct     1104
Leu Gly Ser Thr Gly Arg Ser Phe Val Val Gly Tyr Gly Val Asn Pro
        355                 360                 365 cct caa cat cct cat cac aga act gct cac ggt tca tgg aca gat caa     1152
Pro Gln His Pro His His Arg Thr Ala His Gly Ser Trp Thr Asp Gln
    370                 375                 380 atg act tca cca aca tac cac agg cat act att tat ggt gcg ttg gta     1200
Met Thr Ser Pro Thr Tyr His Arg His Thr Ile Tyr Gly Ala Leu Val
385                 390                 395                 400 gga gga ccg gat aat gca gat ggc tat act gat gaa ata aac aat tat     1248
Gly Gly Pro Asp Asn Ala Asp Gly Tyr Thr Asp Glu Ile Asn Asn Tyr
                405                 410                 415 gtc aat aat gaa ata gcc tgc gat tat aat gcc gga ttt aca ggt gca     1296
Val Asn Asn Glu Ile Ala Cys Asp Tyr Asn Ala Gly Phe Thr Gly Ala
            420                 425                 430 ctt gca aaa atg tac aag cat tct ggc gga gat ccg att cca aac ttc     1344
Leu Ala Lys Met Tyr Lys His Ser Gly Gly Asp Pro Ile Pro Asn Phe
        435                 440                 445 aag gct atc gaa aaa ata acc aac gat gaa gtt att ata aag gca ggt     1392
Lys Ala Ile Glu Lys Ile Thr Asn Asp Glu Val Ile Ile Lys Ala Gly
    450                 455                 460 ttg aat tca act ggc cct aac tac act gaa atc aag gct gtt gtt tat     1440
Leu Asn Ser Thr Gly Pro Asn Tyr Thr Glu Ile Lys Ala Val Val Tyr
465                 470                 475                 480 aac cag aca gga tgg cct gca aga gtt acg gac aag ata tca ttt aaa     1488
Asn Gln Thr Gly Trp Pro Ala Arg Val Thr Asp Lys Ile Ser Phe Lys
                485                 490                 495 tat ttt atg gac ttg tct gaa att gta gca gca gga att gat cct tta     1536
Tyr Phe Met Asp Leu Ser Glu Ile Val Ala Ala Gly Ile Asp Pro Leu
            500                 505                 510 agc ctt gta aca agt tca aat tat tct gaa ggt aag aat act aag gtt     1584
Ser Leu Val Thr Ser Ser Asn Tyr Ser Glu Gly Lys Asn Thr Lys Val
        515                 520                 525 tcc ggt gtg ttg cca tgg gat gtt tca aat aat gtt tac tat gta aat     1632
Ser Gly Val Leu Pro Trp Asp Val Ser Asn Asn Val Tyr Tyr Val Asn
    530                 535                 540 gtt gat ttg aca gga gaa aat atc tac cca ggc ggt cag tct gcg tgc     1680
Val Asp Leu Thr Gly Glu Asn Ile Tyr Pro Gly Gly Gln Ser Ala Cys
545                 550                 555                 560 aga cga gaa gtt cag ttc aga att gcc gca cca cag gga aga aga tat     1728
Arg Arg Glu Val Gln Phe Arg Ile Ala Ala Pro Gln Gly Arg Arg Tyr
                565                 570                 575 tgg aat ccg aaa aat gat ttc tca tat gat gga tta cca acc acc agt     1776
Trp Asn Pro Lys Asn Asp Phe Ser Tyr Asp Gly Leu Pro Thr Thr Ser
            580                 585                 590 act gta aat acg gtt acc aac ata cct gtt tat gat aac ggc gta aaa     1824
Thr Val Asn Thr Val Thr Asn Ile Pro Val Tyr Asp Asn Gly Val Lys
        595                 600                 605 gta ttt ggt aac gaa ccc gca ggt gga tca gaa ccc ggc aca aag ctc     1872
```

```
Val Phe Gly Asn Glu Pro Ala Gly Gly Ser Glu Pro Gly Thr Lys Leu
        610                 615                 620 gtt cct aca tgg ggc gat aca aac tgc gac ggc gtt gta aat gtt gct    1920
Val Pro Thr Trp Gly Asp Thr Asn Cys Asp Gly Val Val Asn Val Ala
625                 630                 635                 640 gac gta gta gtt ctt aac aga ttc ctc aac gat cct aca tat tct aac    1968
Asp Val Val Val Leu Asn Arg Phe Leu Asn Asp Pro Thr Tyr Ser Asn
                645                 650                 655 att act gat cag ggt aag gtt aac gca gac gtt gtt gat cct cag gat    2016
Ile Thr Asp Gln Gly Lys Val Asn Ala Asp Val Val Asp Pro Gln Asp
            660                 665                 670 aag tcc ggc gca gca gtt gat cct gca ggc gta aag ctc aca gta gct    2064
Lys Ser Gly Ala Ala Val Asp Pro Ala Gly Val Lys Leu Thr Val Ala
        675                 680                 685 gac tct gag gca atc ctc aag gct atc gtt gaa ctc atc aca ctt cct    2112
Asp Ser Glu Ala Ile Leu Lys Ala Ile Val Glu Leu Ile Thr Leu Pro
690                 695                 700 caa tga                                                             2118
Gln
705

<210> SEQ ID NO 6
<211> LENGTH: 705
<212> TYPE: PRT
<213> ORGANISM: Artificial Sequence
<220> FEATURE:
<223> OTHER INFORMATION: Synthetic Construct

<400> SEQUENCE: 6

Met Gly Thr Tyr Asn Tyr Gly Glu Ala Leu Gln Lys Ser Ile Met Phe
1               5                   10                  15

Tyr Glu Phe Gln Arg Ser Gly Asp Leu Pro Ala Asp Lys Arg Asp Asn
                20                  25                  30

Trp Arg Asp Asp Ser Gly Met Lys Asp Gly Ser Asp Val Gly Val Asp
            35                  40                  45

Leu Thr Gly Gly Trp Tyr Asp Ala Gly Asp His Val Lys Phe Asn Leu
        50                  55                  60

Pro Met Ser Tyr Thr Ser Ala Met Leu Ala Trp Ser Leu Tyr Glu Asp
65                  70                  75                  80

Lys Asp Ala Tyr Asp Lys Ser Gly Gln Thr Lys Tyr Ile Met Asp Gly
                85                  90                  95

Ile Lys Trp Ala Asn Asp Tyr Phe Ile Lys Cys Asn Pro Thr Pro Gly
            100                 105                 110

Val Tyr Tyr Tyr Gln Val Gly Asp Gly Lys Asp His Ser Trp Trp
        115                 120                 125

Gly Pro Ala Glu Val Met Gln Met Glu Arg Pro Ser Phe Lys Val Asp
    130                 135                 140

Ala Ser Lys Pro Gly Ser Ala Val Cys Ala Ser Thr Ala Ala Ser Leu
145                 150                 155                 160

Ala Ser Ala Ala Val Val Phe Lys Ser Ser Asp Pro Thr Tyr Ala Glu
                165                 170                 175

Lys Cys Ile Ser His Ala Lys Asn Leu Phe Asp Met Ala Asp Lys Ala
            180                 185                 190

Lys Ser Asp Ala Gly Tyr Thr Ala Ala Ser Gly Tyr Tyr Ser Ser Ser
        195                 200                 205

Ser Phe Tyr Asp Asp Leu Ser Trp Ala Ala Val Trp Leu Tyr Leu Ala
    210                 215                 220
```

```
Thr Asn Asp Ser Thr Tyr Leu Asp Lys Ala Glu Ser Tyr Val Pro Asn
225                 230                 235                 240

Trp Gly Lys Glu Gln Gln Thr Asp Ile Ile Ala Tyr Lys Trp Gly Gln
            245                 250                 255

Cys Trp Asp Asp Val His Tyr Gly Ala Glu Leu Leu Leu Ala Lys Leu
            260                 265                 270

Thr Asn Lys Gln Leu Tyr Lys Asp Ser Ile Glu Met Asn Leu Asp Phe
            275                 280                 285

Trp Thr Thr Gly Val Asn Gly Thr Arg Val Ser Tyr Thr Pro Lys Gly
            290                 295                 300

Leu Ala Trp Leu Phe Gln Trp Gly Ser Leu Arg His Ala Thr Thr Gln
305                 310                 315                 320

Ala Phe Leu Ala Gly Val Tyr Ala Glu Trp Glu Gly Cys Thr Pro Ser
            325                 330                 335

Lys Val Ser Val Tyr Lys Asp Phe Leu Lys Ser Gln Ile Asp Tyr Ala
            340                 345                 350

Leu Gly Ser Thr Gly Arg Ser Phe Val Val Gly Tyr Gly Val Asn Pro
            355                 360                 365

Pro Gln His Pro His His Arg Thr Ala His Gly Ser Trp Thr Asp Gln
370                 375                 380

Met Thr Ser Pro Thr Tyr His Arg His Thr Ile Tyr Gly Ala Leu Val
385                 390                 395                 400

Gly Gly Pro Asp Asn Ala Asp Gly Tyr Thr Asp Glu Ile Asn Asn Tyr
            405                 410                 415

Val Asn Asn Glu Ile Ala Cys Asp Tyr Asn Ala Gly Phe Thr Gly Ala
            420                 425                 430

Leu Ala Lys Met Tyr Lys His Ser Gly Gly Asp Pro Ile Pro Asn Phe
            435                 440                 445

Lys Ala Ile Glu Lys Ile Thr Asn Asp Glu Val Ile Ile Lys Ala Gly
450                 455                 460

Leu Asn Ser Thr Gly Pro Asn Tyr Thr Glu Ile Lys Ala Val Val Tyr
465                 470                 475                 480

Asn Gln Thr Gly Trp Pro Ala Arg Val Thr Asp Lys Ile Ser Phe Lys
            485                 490                 495

Tyr Phe Met Asp Leu Ser Glu Ile Val Ala Ala Gly Ile Asp Pro Leu
            500                 505                 510

Ser Leu Val Thr Ser Ser Asn Tyr Ser Glu Gly Lys Asn Thr Lys Val
            515                 520                 525

Ser Gly Val Leu Pro Trp Asp Val Ser Asn Val Tyr Tyr Val Asn
            530                 535                 540

Val Asp Leu Thr Gly Glu Asn Ile Tyr Pro Gly Gly Gln Ser Ala Cys
545                 550                 555                 560

Arg Arg Glu Val Gln Phe Arg Ile Ala Ala Pro Gln Gly Arg Arg Tyr
            565                 570                 575

Trp Asn Pro Lys Asn Asp Phe Ser Tyr Asp Gly Leu Pro Thr Thr Ser
            580                 585                 590

Thr Val Asn Thr Val Thr Asn Ile Pro Val Tyr Asp Asn Gly Val Lys
            595                 600                 605

Val Phe Gly Asn Glu Pro Ala Gly Gly Ser Glu Pro Gly Thr Lys Leu
            610                 615                 620

Val Pro Thr Trp Gly Asp Thr Asn Cys Asp Gly Val Val Asn Val Ala
625                 630                 635                 640
```

```
Asp Val Val Leu Asn Arg Phe Leu Asn Asp Pro Thr Tyr Ser Asn
            645                 650                 655

Ile Thr Asp Gln Gly Lys Val Asn Ala Asp Val Val Asp Pro Gln Asp
                660                 665                 670

Lys Ser Gly Ala Ala Val Asp Pro Ala Gly Val Lys Leu Thr Val Ala
            675                 680                 685

Asp Ser Glu Ala Ile Leu Lys Ala Ile Val Glu Leu Ile Thr Leu Pro
    690                 695                 700

Gln
705

<210> SEQ ID NO 7
<211> LENGTH: 1341
<212> TYPE: DNA
<213> ORGANISM: Artificial Sequence
<220> FEATURE:
<223> OTHER INFORMATION: Fusion construct enzyme-dockerin
<220> FEATURE:
<221> NAME/KEY: CDS
<222> LOCATION: (1)..(1341)

<400> SEQUENCE: 7
```

| | | |
|---|---|---|
| atg gca ggt gtg cct ttt aac aca aaa tac ccc tat ggt cct act tct<br>Met Ala Gly Val Pro Phe Asn Thr Lys Tyr Pro Tyr Gly Pro Thr Ser<br>1               5                  10                  15 | 48 |
| att gcc gat aat cag tcg gaa gta act gca atg ctc aaa gca gaa tgg<br>Ile Ala Asp Asn Gln Ser Glu Val Thr Ala Met Leu Lys Ala Glu Trp<br>            20                  25                  30 | 96 |
| gaa gac tgg aag agc aag aga att acc tcg aac ggt gca gga gga tac<br>Glu Asp Trp Lys Ser Lys Arg Ile Thr Ser Asn Gly Ala Gly Gly Tyr<br>        35                  40                  45 | 144 |
| aag aga gta cag cgt gat gct tcc acc aat tat gat acg gta tcc gaa<br>Lys Arg Val Gln Arg Asp Ala Ser Thr Asn Tyr Asp Thr Val Ser Glu<br>    50                  55                  60 | 192 |
| ggt atg gga tac gga ctt ctt ttg gcg gtt tgc ttt aac gaa cag gct<br>Gly Met Gly Tyr Gly Leu Leu Leu Ala Val Cys Phe Asn Glu Gln Ala<br>65                  70                  75                  80 | 240 |
| ttg ttt gac gat tta tac cgt tac gta aaa tct cat ttc aat gga aac<br>Leu Phe Asp Asp Leu Tyr Arg Tyr Val Lys Ser His Phe Asn Gly Asn<br>                85                  90                  95 | 288 |
| gga ctt atg cac tgg cac att gat gcc aac aac aat gtt aca agt cat<br>Gly Leu Met His Trp His Ile Asp Ala Asn Asn Asn Val Thr Ser His<br>            100                 105                 110 | 336 |
| gac ggc ggc gac ggt gcg gca acc gat gct gat gag gat att gca ctt<br>Asp Gly Gly Asp Gly Ala Ala Thr Asp Ala Asp Glu Asp Ile Ala Leu<br>        115                 120                 125 | 384 |
| gcg ctc ata ttt gcg gac aag tta tgg ggt tct tcc ggt gca ata aac<br>Ala Leu Ile Phe Ala Asp Lys Leu Trp Gly Ser Ser Gly Ala Ile Asn<br>    130                 135                 140 | 432 |
| tac ggg cag gaa gca agg aca ttg ata aac aat ctt tac aac cat tgt<br>Tyr Gly Gln Glu Ala Arg Thr Leu Ile Asn Asn Leu Tyr Asn His Cys<br>145                 150                 155                 160 | 480 |
| gta gag cat gga tcc tat gta tta aag ccc ggt gac aga tgg gga ggt<br>Val Glu His Gly Ser Tyr Val Leu Lys Pro Gly Asp Arg Trp Gly Gly<br>                165                 170                 175 | 528 |
| tca tca gta aca aac ccg tca tat ttt gcg cct gca tgg tac aaa gtg<br>Ser Ser Val Thr Asn Pro Ser Tyr Phe Ala Pro Ala Trp Tyr Lys Val<br>            180                 185                 190 | 576 |
| tat gct caa tat aca gga gac aca aga tgg aat caa gtg gcg gac aag<br>Tyr Ala Gln Tyr Thr Gly Asp Thr Arg Trp Asn Gln Val Ala Asp Lys | 624 |

```
                195                 200                 205
tgt tac caa att gtt gaa gaa gtt aag aaa tac aac aac gga acc ggc      672
Cys Tyr Gln Ile Val Glu Glu Val Lys Lys Tyr Asn Asn Gly Thr Gly
    210                 215                 220 ctt gtt cct gac tgg tgt act gca agc gga act ccg gca agc ggt cag      720
Leu Val Pro Asp Trp Cys Thr Ala Ser Gly Thr Pro Ala Ser Gly Gln
225                 230                 235                 240 agt tac gac tac aaa tat gat gct aca cgt tac ggc tgg aga act gcc      768
Ser Tyr Asp Tyr Lys Tyr Asp Ala Thr Arg Tyr Gly Trp Arg Thr Ala
                245                 250                 255 gtg gac tat tca tgg ttt ggt gac cag aga gca aag gca aac tgc gat      816
Val Asp Tyr Ser Trp Phe Gly Asp Gln Arg Ala Lys Ala Asn Cys Asp
            260                 265                 270 atg ctg acc aaa ttc ttt gcc aga gac ggg gca aaa gga atc gtt gac      864
Met Leu Thr Lys Phe Phe Ala Arg Asp Gly Ala Lys Gly Ile Val Asp
        275                 280                 285 gga tac aca att caa ggt tca aaa att agc aac aat cac aac gca tca      912
Gly Tyr Thr Ile Gln Gly Ser Lys Ile Ser Asn Asn His Asn Ala Ser
    290                 295                 300 ttt ata gga cct gtt gcg gca gca agt atg aca ggt tac gat ttg aac      960
Phe Ile Gly Pro Val Ala Ala Ala Ser Met Thr Gly Tyr Asp Leu Asn
305                 310                 315                 320 ttt gca aag gaa ctt tat agg gag act gtt gct gta aag gac agt gaa     1008
Phe Ala Lys Glu Leu Tyr Arg Glu Thr Val Ala Val Lys Asp Ser Glu
                325                 330                 335 tat tac gga tat tac gga aac agc ttg aga ctg ctc act ttg ttg tac     1056
Tyr Tyr Gly Tyr Tyr Gly Asn Ser Leu Arg Leu Leu Thr Leu Leu Tyr
            340                 345                 350 ata aca gga aac ttc ccg aat cct ttg agt gac ctt tcc ggc caa ccg     1104
Ile Thr Gly Asn Phe Pro Asn Pro Leu Ser Asp Leu Ser Gly Gln Pro
        355                 360                 365 aca cca ccg tcg aat ccg aca cct tca ttg cct cct cag gtt gtt tac     1152
Thr Pro Pro Ser Asn Pro Thr Pro Ser Leu Pro Pro Gln Val Val Tyr
    370                 375                 380 ggt gat gta aat ggc gac ggt aat gtt aac tcc act gat ttg act atg     1200
Gly Asp Val Asn Gly Asp Gly Asn Val Asn Ser Thr Asp Leu Thr Met
385                 390                 395                 400 tta aaa aga tat ctg ctg aag agt gtt acc aat ata aac aga gag gct     1248
Leu Lys Arg Tyr Leu Leu Lys Ser Val Thr Asn Ile Asn Arg Glu Ala
                405                 410                 415 gca gac gtt aat cgt gac ggt gcg att aac tcc tct gac atg act ata     1296
Ala Asp Val Asn Arg Asp Gly Ala Ile Asn Ser Ser Asp Met Thr Ile
            420                 425                 430 tta aag aga tat ctg ata aag agc ata ccc cac cta cct tat tag         1341
Leu Lys Arg Tyr Leu Ile Lys Ser Ile Pro His Leu Pro Tyr
        435                 440                 445

<210> SEQ ID NO 8
<211> LENGTH: 446
<212> TYPE: PRT
<213> ORGANISM: Artificial Sequence
<220> FEATURE:
<223> OTHER INFORMATION: Synthetic Construct

<400> SEQUENCE: 8

Met Ala Gly Val Pro Phe Asn Thr Lys Tyr Pro Tyr Gly Pro Thr Ser
1               5                   10                  15

Ile Ala Asp Asn Gln Ser Glu Val Thr Ala Met Leu Lys Ala Glu Trp
            20                  25                  30
```

```
Glu Asp Trp Lys Ser Lys Arg Ile Thr Ser Asn Gly Ala Gly Gly Tyr
         35                  40                  45

Lys Arg Val Gln Arg Asp Ala Ser Thr Asn Tyr Asp Thr Val Ser Glu
 50                  55                  60

Gly Met Gly Tyr Gly Leu Leu Leu Ala Val Cys Phe Asn Glu Gln Ala
 65                  70                  75                  80

Leu Phe Asp Asp Leu Tyr Arg Tyr Val Lys Ser His Phe Asn Gly Asn
                 85                  90                  95

Gly Leu Met His Trp His Ile Asp Ala Asn Asn Val Thr Ser His
                100                 105                 110

Asp Gly Gly Asp Gly Ala Ala Thr Asp Ala Asp Glu Asp Ile Ala Leu
                115                 120                 125

Ala Leu Ile Phe Ala Asp Lys Leu Trp Gly Ser Ser Gly Ala Ile Asn
130                 135                 140

Tyr Gly Gln Glu Ala Arg Thr Leu Ile Asn Asn Leu Tyr Asn His Cys
145                 150                 155                 160

Val Glu His Gly Ser Tyr Val Leu Lys Pro Gly Asp Arg Trp Gly Gly
                165                 170                 175

Ser Ser Val Thr Asn Pro Ser Tyr Phe Ala Pro Ala Trp Tyr Lys Val
                180                 185                 190

Tyr Ala Gln Tyr Thr Gly Asp Thr Arg Trp Asn Gln Val Ala Asp Lys
                195                 200                 205

Cys Tyr Gln Ile Val Glu Val Lys Lys Tyr Asn Asn Gly Thr Gly
210                 215                 220

Leu Val Pro Asp Trp Cys Thr Ala Ser Gly Thr Pro Ala Ser Gly Gln
225                 230                 235                 240

Ser Tyr Asp Tyr Lys Tyr Asp Ala Thr Arg Tyr Gly Trp Arg Thr Ala
                245                 250                 255

Val Asp Tyr Ser Trp Phe Gly Asp Gln Arg Ala Lys Ala Asn Cys Asp
                260                 265                 270

Met Leu Thr Lys Phe Phe Ala Arg Asp Gly Ala Lys Gly Ile Val Asp
        275                 280                 285

Gly Tyr Thr Ile Gln Gly Ser Lys Ile Ser Asn Asn His Asn Ala Ser
290                 295                 300

Phe Ile Gly Pro Val Ala Ala Ala Ser Met Thr Gly Tyr Asp Leu Asn
305                 310                 315                 320

Phe Ala Lys Glu Leu Tyr Arg Glu Thr Val Ala Val Lys Asp Ser Glu
                325                 330                 335

Tyr Tyr Gly Tyr Tyr Gly Asn Ser Leu Arg Leu Leu Thr Leu Leu Tyr
                340                 345                 350

Ile Thr Gly Asn Phe Pro Asn Pro Leu Ser Asp Leu Ser Gly Gln Pro
                355                 360                 365

Thr Pro Pro Ser Asn Pro Thr Pro Ser Leu Pro Pro Gln Val Val Tyr
370                 375                 380

Gly Asp Val Asn Gly Asp Gly Asn Val Asn Ser Thr Asp Leu Thr Met
385                 390                 395                 400

Leu Lys Arg Tyr Leu Leu Lys Ser Val Thr Asn Ile Asn Arg Glu Ala
                405                 410                 415

Ala Asp Val Asn Arg Asp Gly Ala Ile Asn Ser Ser Asp Met Thr Ile
                420                 425                 430

Leu Lys Arg Tyr Leu Ile Lys Ser Ile Pro His Leu Pro Tyr
                435                 440                 445
```

ENGINEERING OF YEAST FOR CELLULOSIC ETHANOL PRODUCTION

CROSS REFERENCE TO RELATED APPLICATIONS

This application is a U.S. National Stage Application filed under 35 U.S.C. §371 and claims priority to International Application Serial No. PCT/US09/64491, filed Nov. 14, 2009, which claims priority under 35 U.S.C. §119 from Provisional Application Ser. No. 61/115,068, filed Nov. 15, 2008, the disclosures of which are incorporated herein by reference.

TECHNICAL FIELD

The disclosure provides designer cellulosomes. The disclosure also provides methods for efficient hydrolysis of cellulosic material and more particularly for the generating of ethanol.

BACKGROUND

Several billion gallons of renewable fuel must be produced by 2012 with most of that produced as biofuel using renewable biomass. In particular, bioethanol from renewable sources provides an attractive form of alternative energy. It has been estimated that the amount of ethanol needed as transportation fuel will reach 7.5 billion gallons. However, the total capacity of ethanol production in this country is only about 4.2 billion gallons, significantly lower than the required amount.

SUMMARY

The disclosure provides a synthetic yeast consortium for direct fermentation of cellulose to ethanol with productivity, yield and final concentration close to that from glucose fermentation. The engineering strategy described herein uses the efficiency of hydrolysis and synergy among multi-cellulases. To emulate the success of a natural cellulose hydrolysis mechanism, a complex cellulosome structure is assembled on a yeast cell surface using a constructed yeast consortium, which enables the ethanol-producing strains to utilize cellulose and concomitantly ferment it to ethanol. More importantly, by organizing these cellulases in an ordered structure, enhanced synergy increases the hydrolysis, and thereby the production of ethanol.

The disclosure provides a culture comprising: a first recombinant yeast strain comprising an anchoring scaffoldin (anScaff); a second recombinant yeast strain comprising an adaptor scaffoldins comprising a plurality of cohesin domains and at least one cellulose binding domain (CBD); and at least one recombinant yeast strain comprising a plurality of secreted dockerin-tagged cellulases. In one embodiment, the yeast strains are cultured under conditions wherein the anchoring scaffoldin, the adaptor scaffoldin comprising the cohesion domains and the plurality of dockerin-tagged cellulases associated to generate an engineered cellulosome. In yet another embodiment, the cellulases are selected from endoglucanases, exoglucanases, β-glucosidase, and xylanase. In a further embodiment, the dockerin-tagged cellulase is engineered to comprise an leader sequence for secretion of the dockerin-tagged cellulase.

The disclosure provides a recombinant yeast strain comprising a heterologous plynucleotide encoding an anchoring scaffoldin.

The disclosure also provides a recombinant yeast strain comprising a heterologous polynucleotide encoding an adaptor scaffoldin comprising a plurality of cohesin domains and at least one cellulose binding domain (CBD).

The disclosure provides a recombinant yeast strain comprising at least one heterologous polynucleotide encoding a secreted dockerin-tagged cellulase.

The disclosure provides a culture comprising a recombinant yeast strain at least two yeast strains comprising a portion of a functional cellulosome, wherein upon co-culture a functional cellulosome is generated.

The disclosure also provides a yeast culture comprising at least two recombinant strains of yeast wherein the culture produces a designer cellulosome, and wherein the yeast culture catabolizes cellulosic material to produce a biofuel.

The disclosure also provides a method of producing a biofuel comprising: culturing the yeast of any as described above in a fermentation broth comprising a cellulosic material, wherein the microorganism produces the biofuel metabolite.

The disclosure further provides a method of designing a cellulosome comprising identifying the cellulosic substrate, identifying at least one enzyme useful for degradation of the cellulosic material, recombinantly engineering a dockerin peptide to the enzyme, cloning a polynucleotide encoding the dockerin-linked enzyme into a microorganism, culturing the microorganism in a culture of at least one additional microorganism expressing a scaffoldin having a plurality of cohesion domains and a cellulosic binding domain, wherein the cohesion and dockerin a compatible and culturing the microorganisms to express the scaffoldin and dockerin-linked enzymes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 5A-D show graphs of cellusome activity. Production of glucose (A) and reducing sugars (B) from the hydrolysis of PASC by free enzymes and by surface-displayed cellulosomes. Reactions were conducted either with different cellulase pairs (CelE-Dc [Ec], CelA-Dt [At], or _-glucosidase-Df [BglA]) docked on the displayed Scaf-ctf protein or with the corresponding purified cellulases. Cells displaying only Scaf-ctf were used as controls. (C) Activity associated with cells and (D) activity in the medium at different initial OD ratios.

DETAILED DESCRIPTION

Figure 1A:
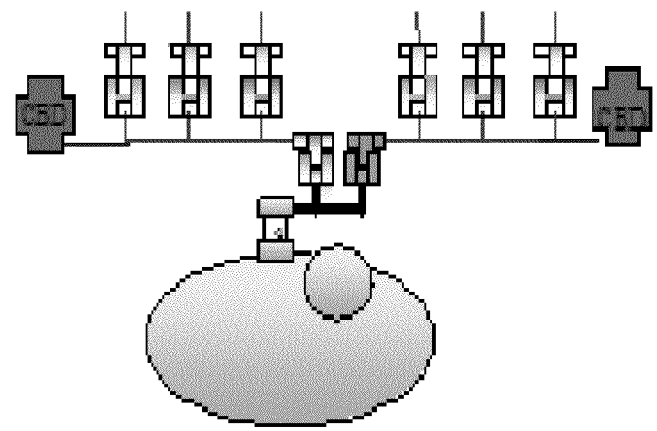
FIG. 1A-B shows functional assembly of minicellulosomes on the yeast cell surface. A trifunctional scaffoldin (Scaf-ctf) consisting of an internal CBD flanked by three divergent cohesin (C) domains from *C. thermocellum* (t), *C. cellulolyticum* (c), and *R. flavefaciens* (f) was displayed on the yeast cell surface. Three different cellulases (E1, E2, and E3) fused with the corresponding dockerin domain (either Dt, Dc, or Df) were expressed in *E. coli*. Cell lysates containing these cellulases were mixed with yeast cells displaying Scaf-ctf for the functional assembly of the minicellulosome.

As used herein and in the appended claims, the singular forms "a," "and," and "the" include plural referents unless the context clearly dictates otherwise. Thus, for example, reference to "a probe" includes a plurality of such probes and reference to "the primer" includes reference to one or more primers and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Biomass represents an inexpensive feedstock for sustainable bioethanol production. Among the three biological events that occur during the conversion of cellulose to ethanol, i.e., enzyme production, polysaccharide hydrolysis, and sugar fermentation, cellulose hydrolysis is widely recognized as the key step in making bioconversion economically competitive. In addition, it is believed that a significant cost reduction can be achieved when two or more steps are combined, such as in CBP. To achieve this goal, the disclosure provides methods and cellular compositions comprising a functional assembly of a minicellulosome on a yeast cell surface. The minicellulosome was engineered to render the ethanologenic microbe cellulolytic.

In one embodiment, the disclosure achieves the method and composition by first engineering a chimeric minicellulosome containing three dockerin cohesion pairs from different species on the yeast cell surface. Immunofluorescence microscopy showed the successful translocation of the miniscaffoldin on the yeast cell surface, and the functionality of the cohesin domains was retained by observing the successful assembly of the corresponding dockerin-tagged cellulases. Since the specificity of the dockerin-cohesin pairs is preserved, it is possible to direct any enzymatic subunit to a specified position within a modular scaffoldin by tagging with the designated dockerin.

The disclosure further demonstrates a synergistic effect on cellulose hydrolysis compared with that of free enzymes.

In the compositions and methods of the disclosure the displayed minicellulosome retained this key characteristic. Interestingly, the level of synergy increased with an increasing number of cellulases docked on the cell surface. This synergistic effect was preserved even when a new minicellulosome comprising a β-glucosidase (BglA), an endoglucanase (At), and an exoglucanase (Ec) was assembled on the yeast cell surface.

The disclosure further demonstrates that the methods and compositions of the disclosure are useful at ethanol production. Cellulose hydrolysis and ethanol production were tested with both free enzymes and a displayed minicellulosome. Independent of the number of cellulases incorporated in the minicellulosome, similar levels of enhancement of cellulose hydrolysis, as well as ethanol production, were detected. The ethanol production achieved, in particular, was more than 2.6-fold higher than that of the culture in which all three cellulases were added as free enzymes. This, when combined with an ethanol yield close to 95% of the theoretical maximum, makes this an efficient process for direct fermentation of cellulose to ethanol.

Current production processes for using crops such as sugar cane and cornstarch for bioethanol production are well established. However, since the cost of raw materials can be as high as 40% of the overall process, utilization of a cheaper substrate would render bioethanol more competitive with fossil fuel (Zaldivar et al, 2001). Among the different forms of biomass, lignocellulosic biomass is particularly well-suited for energy applications because of its large-scale availability, low cost and environmentally benign production (Lynd et al, 1999). This natural and abundant polymer is found as agricultural waste (wheat straw, corn stalks, soybean residues), industrial waste (pulp and paper industry), forestry residues, and municipal solid waste. Many energy production and utilization cycles based on cellulosic biomass have near-zero greenhouse gas emissions on a life-cycle basis (Lynd et al, 2005).

The primary obstacle impeding the more widespread production of energy from biomass is the absence of a low-cost technology for overcoming the recalcitrance of these materials (Lynd et al, 2008). For cellulose to be amenable to fermentation, it needs to undergo several treatments to release its monomeric sugars (Zaldivar et al, 2001). Two main steps are: (1) pretreatments that remove lignin and exposes cellulose for enzymatic degradation, and (2) an enzymatic treatment to generate glucose from cellulose before fermentation. The high cost of cellulases needed for cellulose hydrolysis is one of the major obstacles in the quest for an economically feasible cellulose-based bioethanol process (McBride at al, 2005).

Although the cost of bioethanol production can become more competitive by combining the hydrolysis and fermentation steps in simultaneous saccharification and cofermentation (SSCF) of both hexoses and pentoses, it has been shown that the overall cost can be even further reduced by 4-fold using a one-step "consolidated" bioprocessing (CBP) of lignocellulose to bioethanol, where cellulase production, cellulose hydrolysis and sugar fermentation can be mediated by a single microorganism or microbial consortium. An ideal microorganism for CBP should possess the capability of simultaneous cellulose saccharification and ethanol fermentation. One attractive candidate is *Saccharomyces cerevisiae*, which is widely used for industrial ethanol production due to its high ethanol productivity and high inherent ethanol tolerance.

However, due to energetic limitations under anaerobic conditions, only a limited amount of cellulases can often be secreted, resulting in relatively low rates of cellulose hydrolysis. It is believed that, for a process to be viable economically, it must have productivity greater than 1 g/l/hr (Zaldivar et al, 2001). For example, where cellulases are displayed on yeast surface the productivity (0.075 g/l/hr) was more than one order of magnitude lower than strains fermenting glucose.

Unfortunately, substantial improvement in cellulose hydrolysis may not come from simply increasing the amount of enzymes secreted to the medium or displayed on the surface, which is obviously limited under anaerobic conditions. The key to improving hydrolysis is, perhaps, to increase the catalytic efficiency by maximizing the synergy with limited amount of enzymes. Recently, it has been demonstrated that the use of ternary cellulose-enzyme-microbe complexes yields much higher rates of cellulose hydrolysis than using binary cellulose-enzyme complexes (Lu et al, 2006). This enzyme-microbe synergy requires the presence of metabolically active *Clostridium thermocellum* displaying cellulosome and appears to be a surface phenomenon involving microbial adhesion onto the cellulose. The 2 to 4-fold synergistic effect observed is significant in decreasing the cost for cellulose hydrolysis.

An understanding of the role of cellulosomes can be viewed as two distinct mechanisms to tackle the recalcitrant cellulose. Aerobic microbes (such as *Trichoderma reesei*) produce copious amounts of soluble hydrolytic enzymes that synergistically breakdown cellulosic materials (Wilson, 2004; Bayer et al., 2000). In contrast, anaerobic organisms, due to energetic constraints, can only produce a limited amount of enzymes. Therefore, in response, anaerobic organism have become more efficient and have developed an elaborately structured enzyme complex, called a cellulosome, to maximize catalytic efficiency (Bayer et al., 2004; Doi and Kosugi, 2004; Demain et al., 2005). This self-assembled system brings multiple enzymes in close proximity to the substrate, and provides a structure that ensures high local concentration and the correct ratio and orders of the enzymes, thereby maximizing synergy. Consequently, it has a much higher catalytic efficiency than soluble enzymes present in a non-organized fashion. A study showed that the structure endowed an enzyme activity increase of up to 50 times (Johnson et al., 1982).

Figure 1B:
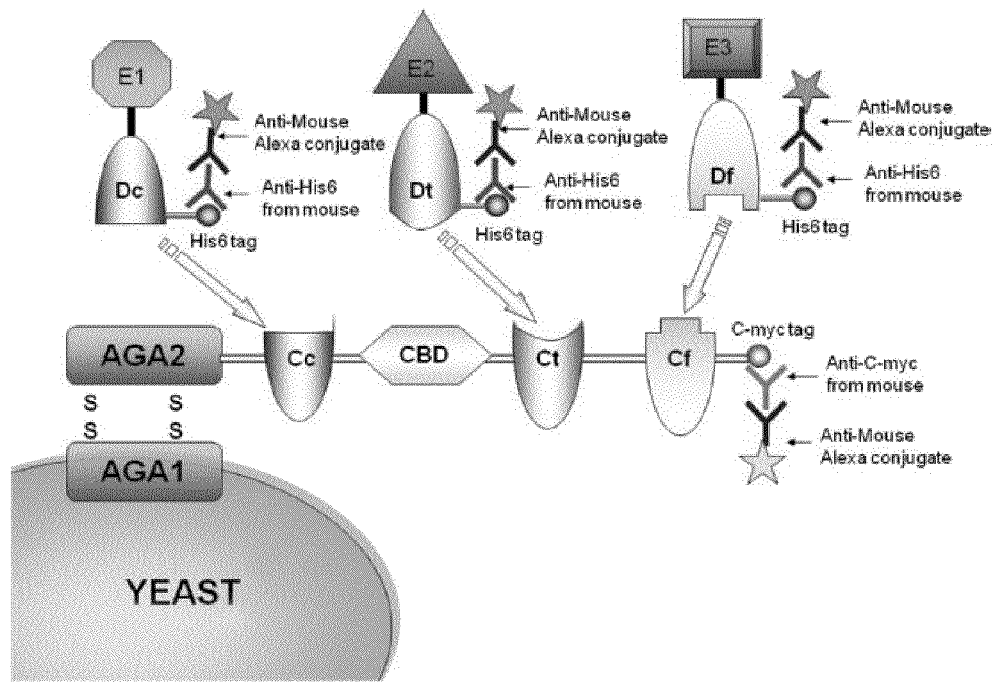

Cellulosomes are self-assembled multi-enzyme complexes presented on the anaerobes' cell surface and are dedicated to cellulose depolymerization. The major component of these macromolecule complexes is a structural scaffoldin consists of at least one cellulose binding domain (CBD) and repeating cohesin domains, which are docked individually with a cellulase tagged with a dockerin domain (FIG. 1). The CBD serves as a targeting agent to direct the catalytic domains to the cellulose substrates. The specific protein-protein, or complementary cohesin-dockerin interaction, provides the mechanism for position-specific self-assembly. Within a given species, the dockerin component appears to bind to all of the cohesins with similar affinity, thus suggesting a random incorporation of the enzymes in the cellulosome. The relative abundance of the catalytic subunits in the cellulosomes is assumed to reflect the level of expression of the corresponding genes as such as in the case of *C. cellulolyticum* using a genetic approach. These cohesin and dockerin modules are species-specific and do not cross interact (Carvalho et al, 2005; Pages et al, 1997). However, recently studies confirmed the presence of other Type II and Type III cohesin/dockerin pairs within a given species in additional to the original Type I mentioned above. These additional pairs are structurally very different and have been shown to possess different specificities to the Type I cohesin/dockerin pairs (Haimovitz et al, 2008).

The multi-enzyme complex attaches both to the cell envelope and to the substrate, mediating the proximity of the cells to the cellulose (Schwarz, 2001). The ability for substrate-targeting is one of the reasons for increased catalytic efficiency. In addition, the production of cellulosome has a number of advantages over soluble enzymes, for hydrolysis of cellulose:

1. Synergism is optimized due to the proximity of enzyme components,
2. Non-productive adsorption is avoided by the optimal spacing of components,
3. Competitiveness in binding to a limited number of binding sites is avoided by binding the whole cellulosome complex to a single site through a strong binding domain with low specificity,
4. A halt in hydrolysis on depletion of one structural type of cellulose at the site of adsorption is avoided by the presence of other enzymes with different specificity.

The disclosure provides a recombinant yeast expressing cellulosomal structures. Bioenergetic benefits and synergy are achieved when the cellulosomal structures are displayed onto a microorganism having the ability to ferment biomass to ethanol such as yeast (e.g. *S. cerevisiae*). The recombinant organisms of the disclosure are useful for bioethanol production as fewer enzymes are needed. Additionally, since glucosidase is typically subjected to product inhibition, presence of active glucose-metabolizing cells should further increase the overall hydrolysis rate. The disclosure provides engineered yeast comprising a consortium capable of displaying the highly efficient cellulose-degrading cellulosome structures for one-step CBP of cellulosic materials.

The functional presentation of various cellulose-binding domains and catalytic subunits in a cellulosome provides improved cellulose hydrolysis over free enzymes as a consequence of the synergistic action among the different components. Because of the modular nature of the cellulosomal subunits the disclosure provides artificial cellulsomes useful in generating biofuels from aerobic organisms at efficiency similar to anaerobic organisms. For example, the disclosure demonstrates that usefulness of a recombinant CBD in yeast using a trifunctional chimeric scaffoldin containing cohesins from a plurality of species. The trifunctional chimeric scaffoldin was constructed and each type of cohesion module was shown to bind specifically to the corresponding dockerin-borne cellulolytic enzymes in vitro. The resulting 6-fold improvement in cellulose hydrolysis over similar free enzymes demonstrates that the "designer cellulosome" of the disclosure can be similarly exploited for whole-cell hydrolysis of cellulose and ethanol production when expressed by yeast (e.g., *S. cerevisiae*). The disclosure demonstrates that by displaying a mini-scaffoldin onto the yeast surface a designer cellulosome was obtain. In one embodiment, the resulting yeast cells when tagged with three different dockerin-tagged cellulases were shown to degrade cellulose up to 3-fold faster.

Figure 2:
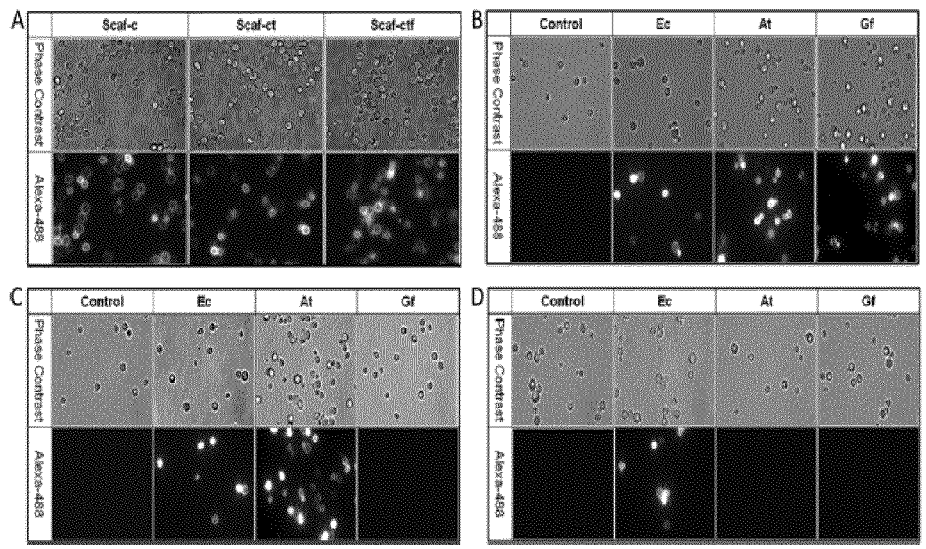
FIG. 2A-D shows phase-contrast and immunofluorescence micrographs of yeast cells displaying minicellulosomes. (A) Cells displaying either scaffoldin Scaf-c, Sacf-ct, or Sacf-ctf. Functional assembly of three dockerin-tagged cellulases (CelE-Dc [Ed], CelA-Dt [At], or CelG-Df [Gf]) on cells displaying (B) Sacf-ctf, (C) Sacf-ct, or (D) Scaf-c. Cells were probed with either anti-c-Myc or anti-c-His6 serum and fluorescently stained with a goat anti-mouse IgG conjugated with Alexa Fluor 488. Cells displaying only the scaffoldins were used as controls.

In yet another embodiment, the disclosure provides a yeast consortium composed of strains with a surface-display anchoring scaffoldin, strains secreting an adapting scaffoldin, and strains secreting dockerin-tagged cellulases (FIG. 2) for the functional presentation of the complex cellulosome structures.

The disclosure demonstrates a synthetic yeast consortium for functional presentation of the complex cellulosome structures and to demonstrate the ability for enhanced ethanol production from cellulose. The disclosure provides recombinant yeast for ethanol production comprising a plurality of cohesions and dockerin polypeptides. Currently, the sequences of more than one hundred different cohesions and dockerins from a dozen cellulosome-producing bacteria are known (Hamiovitz et al., 2008). In one embodiment, the disclosure provides the use of 2, 3, 4, 5, 6, 7, or 8 different cohesin/dockerin pairs for the celluosome assembly.

The disclosure provides a synthetic yeast consortium for direct fermentation of cellulose to ethanol with productivity, yield and final concentration close to that from glucose fermentation. The engineering strategy described herein uses the efficiency of hydrolysis and synergy among multi-cellulases, rather than focusing on the amount of enzymes produced or used. To emulate the success of a natural cellulose hydrolysis mechanism, a complex cellulosome structure is assembled on a yeast cell surface using a constructed yeast consortium, which enables the ethanol-producing strains to utilize cellulose and concomitantly ferment it to ethanol. More importantly, by organizing these cellulases in an ordered structure, the enhanced synergy will increase the hydrolysis, and thereby the production of ethanol.

In one embodiment, the disclosure provides a yeast consortium for surface assembly of a mini-cellulosome structure comprising 2, 3 or more cellulases and demonstrates the feasibility of using the consortium for direct ethanol production from cellulose. In another embodiment, the disclosure provides recombinant yeast for surface-display of one or more of the anchoring scaffoldin, the adaptor scaffoldin, and the dockerin-tagged cellulases.

In one embodiment, the yeast consortium provides a cellulosome comprising a CelA from *Orpinomyces* sp strain PC-2 (see, e.g., Ljungdahl, 2008; Chen et al, 2006, which are incorporated herein by reference), CelC from *Orpinomyces* sp strain PC-2, CelB, CelD, XynA, and 1 B-glucosidase (Voorhorst, 1995). Sequences for the various dockerins, cohesions and cellulases used in the methods and compositions of the disclosure are readily identifiable by one of skill in the art with reference to readily available databases (e.g., GenBank).

In one embodiment, a strain of yeast can be genetically engineered by recombinant DNA techniques to express a polynucleotide comprising one or more structural component for producting a cellulosome, a polynucleotide comprising a structural element linked to a cellulose degrading enzyme (e.g., a cellulase), or a combination of any polynucleotide encoding a cellulosome structural polypeptide or enzyme. Where a single yeast or microorganism does not express a full complement of structural and enzyme polypeptide for production of a complete cellulosome, a combination of two or more recombinant yeast (e.g., a consortium) can be used wherein the two or more recombinant yeast express portions of a cellulsome that upon combination generate a full cellulsome capable of degrading a cellulose material.

For example, in one embodiment, a yeast can be recombinantly engineered to express a trifunctional scaffoldin comprising an internal CBD flanked by three divergent cohesin domains. A first strain recombinant yeast will comprise a plasmid or vector containing one or more (e.g., continuous or separated by linking domains) polynucleotide(s) encoding the CBD flanked by the three divergen cohesin domains. The polynucleotide sequences for a large number of cohesin domains and their corresponding dockerin domains are known in the art. For example, a search of GenBank will identify numerous sequences for cohesin polynucleotide and polypeptides.

A second yeast strain can be recombinantly engineered to contain a plasmid or vector comprising sequence encoding one or more dockerin domains linked to a cellulose degrading enzyme. Upon co-culture each strain expresses the corresponding structural or structural-enzymatic polypeptides. The respective dockerin and cohesin domains bind to one another and form a mini-cellulsome. Again, dockerin and enzyme useful in the methods and compositions of the disclosure are recognized in the art and the corresponding sequences are readily identifiable to one of skill in the art performing a simple search on GenBank. For example, the disclosure provides dockerin-enzyme fusion constructs comprising SEQ ID NOs: 5-7. It will be recognized that variants of each of the enzyme domains of the fusion construct may be used, variants of each of the dockerin domains may be used. For example, polypeptides having 80%-99% identity to SEQ ID NO:6 or 8 (or 80-99% [85%, 90%, 95%, 97%, 98% etc.] identity to the respective enzyme or dockerin domains of the construct) can be used in the methods and compositions of the disclosure so long as the dockerin domain is capable of binding to its respective cohesin domain and the enzyme domain is capable of degrading a cellulose material. Methods for determining percent identity are well known in the art.

A variety of tools are available for the introduction and expression of genes in yeast (such as *S. cerevisiae*), including established vector series (Gietz and Sugino, 1988; Sikorski and Hieter, 1989) and simultaneous or sequential gene integration vectors for the insertion of multiple genes (Wang and Da Silva, 1996; Parekh et al., 1996; Lee and Da Silva, 1997; Lee and Da Silva, 2007).

Plasmids designed to enable combinatorial plasmid-based testing and seamless transition to genomic integration for fine-tuning of gene number and stable long-term expression can be used. This allows rapid and stable strain construction relative to previous methods. The set of 16 plasmids combines four different marker genes (flanked by loxP sites), two different promoters, and two different replication origins (2μ, CEN/ARS). The autonomous vectors allow initial testing of gene combinations on high and/or low copy plasmids. For insertion into the chromosomes, expression polylinker sites adjacent to the selectable markers facilitate polymerase chain reaction amplification of the test gene and selectable marker using primers with outside ends in the desired genomic target sequences. Using this strategy, genes have been successfully inserted into a set of unique locations in the genome with known expression level. The loxP-mediated excision of the selection marker (Sauer, 1987) allows simultaneous marker excision after a group of genes has been integrated, this set of vectors enables both rapid construction and testing of strains, and development of stable engineered strains for use in any complex medium.

For example, using the methods described herein an engineered consortium for cellulose hydrolysis by intercellular complementation is provided and useable in any given ecosystem. The disclosure demonstrates the feasibility of using a yeast consortium for the surface-display of a mini-cellulosome for efficient cellulose hydrolysis. The disclosure demonstrates the correct assembly of secreted At onto the Scaff#3 in a co-culture system. To enable surface display of scaffoldins without galactose induction, expression of the surface anchor AGA1 (FIG. 1) is placed under a constitutive PGK promoter and the 2 copies of the gene cassette integrated.

Various enzymes can be used for to degrade the cellulose material. For example, it has been shown that β-glucosidase is useful for complete degradation of cellulose to glucose. Therefore a well known β-glucosidase BglA from *C. thermocelum* was tagged with the dockerin domain (Bf), produced in *E. coli* and incorporated into the cellulosome structures. The result demonstrates the enhancement effect on glucose liberation by assembling BglA into the mini-cellulosome. Therefore, for the initial demonstration, a mini-cellulosome containing an endoglucanase (At), an exoglucanase (Ec) and BglA are assembled. Secretion of At into the medium using the secretion leader sequence MFα1 was used; a similar strategy is employed for the secretion of Ec and Bf. Secretion of the structure-enzyme can be confirmed using various methods in the art. For example, secretion of Ec and Bf into the medium can be confirmed by Western blotting using a FLAG tag on Ec and a S-tag on Bf. After confirming secretion, the activity of the secreted fusion constructs can be assayed. For example, cellulase activity can be determined using Avicel or cellobiose as the substrate. Finally, cells secreting either Ec and Bf are co-cultured with cells displaying Scaff#3 and the correct assembly of the cellulases onto the cell surface can be confirmed by immunofluorescence microscopy and the ability to hydrolyze Avicel or cellobiose. After confirming the assembly of individual secreted cellulases, the feasibility of assembling the complete mini-cellulosome is performed. To begin with, a co-culture of different yeast strains are tested in SDC medium. The correct assembly of all three cellulases is confirmed by immunofluorescence using a unique tag presented on each one.

In yet another embodiment, a single yeast strain capable of secreting all Ec, At and Bf and a strain displaying Scaff#3 is provided by taking advantage of the rapid sequential integration approach. This method also allows precise regulation of expression by controlling the integrated gene copy number (1 to 5). A small-scale shake-flask cultures are used for varying the initially inoculation cell density from a ratio of 10 to 0.1. The specific culturing conditions that result in the highest number of fluorescence cells with all three tags can then be used. The ability of the consortium to hydrolyze Avicel and the corresponding ethanol production can be measured using standard techniques. For example, cells are grown aerobically in SD medium using glucose as the carbon source. The resuspended cells are then used in anaerobic fermentation (SDC medium) using Avicel or phosphoric acid swollen cellulose (PASC) as the carbon source. Samples of the culture can then be obtain for monitoring the expression level, reducing sugar, intermediates, and cell growth. The ratio of the two different cell populations can be modified to maximize synergy. A coordinated gene expression system leads to the detection of only glucose, whereas accumulation of other products indicate the level of secreted enzymes (or cell population) should be adjusted. For example, if cellobiose is found to accumulate, it indicates that the glucosidase activity is too low relative to the other enzymes and the problem could be easily solved with this strategy by simply increasing the gene dosage for the secreted glucosidase.

To achieve the cellulosome structure as shown in FIG. 9, five additional cohesin/dockerin pairs can be used. Since most of them are species specific, three additional cohesion/dockerin pairs from *B. cellulosolvens* (bc), *Ace. celluloyticus* (ac), and *C. acetobutylicum* (cc) can be used. In addition, Type II cohesion/dockerin pairs from *Clostridium thermocelum* (T) and *Clostridium celluloyticum* (C) are used in conjunction with the Type I pairs (c, t, and f). A feature of the design is the common display of an anchoring scaffoldin, which will enable the surface-display of the complex cellulosome onto all cells except for the strain designed to secrete the adaptor scaffoldins. Since the dockerins used on the cellulolytic enzymes have no cross affinity with the cohesions on the anchoring scaffoldin, no interaction or interference with the translocation machinery is expected. As a result, the resulting consortium will be comprised of cells displaying a functional cellulosome with virtually no carbon source wasted.

To construct the synthetic consortium, different strains are generated. First, a yeast strain designed to display an anchoring scaffoldin (anScaff) containing the cohesin domains from bc and cc is provided. Synthetic oligos coding for two cohesin domains are synthesized and used for plasmid construction. These two domains are joined by a 10 amino acid linker containing GS repeats flanked by a FLAG tag and displayed on the yeast surface using the same GPI anchor. To add the adapter scaffoldins onto the displayed anScaff, a yeast strain designed to secrete two separate adaptor scaffoldins is provided. The first adaptor scaffoldin (adScaff#1) comprises an N-terminus be dockerin flanked by three cohesin domains (t, f, c), one CBD domain, and a C-myc tag. The second adaptor scaffoldin (adScaff#2) comprises an N-terminus cc dockerin flanked by three cohesin domains (ac, type II t and type II c), one CBD domain, and a S-tag. Finally, two different strains are provided to secrete three different dockerin-tagged cellulases each (2 endoglucanases, 2 exoglucanases, one β-glucosidase, and one xylanase) secreted using the MFβ1 leader sequence. A His6 tag is added to each cellulase. In this configuration, the consortium will comprise four strains and three will have the complex cellulosome displayed on the surface.

In addition to At, Ec, and BglA used above, other enzymes from anaerobic fungi that form cellulosome can be used to demonstrate the complex cellulosome structure. This choice is based on the finding that enzymes from these anaerobic fungi have specific activities much higher than enzymes from other sources (Ljungdahl, 2008). Additionally, several of these enzymes were successfully over-expressed in *S. cerevisiae* (Ljungdahl, 2008; Chen et al, 2006), suggesting over expression of enzymes may not be a significant obstacle. Furthermore, since these enzymes are cellulosomal, the structural feature and folding mechanism are likely compatible to the designed structure as compared to other non-cellulosomal enzymes. For example, a cellulosome of the disclosure can comprise CelA and CelC from *Orpinomyces* sp strain PC-2, are both GH family 6 enzymes, possessing both endo and exoglucanase activities; two family 5 cellulases, CelB and CelD, both endoglucanases, are cloned and fused with an appropriate dockerin; the catalytic domain of XynA, a family GH11 xylanase with extremely high activity, is used as the fifth enzyme and a family 1 β-glucosidase from *Piromyces* sp Strain E2 is used as a sixth enzyme.

All of these strains are constructed using the rapid and stable multi-gene integration systems described above; 1 to 5 copies of each gene cassette are integrated in order to optimize the required expression. Expression is under the control of the PGK promoter based on its constitutive nature and the high-level of protein expression. The number of anScaff molecules displayed on the cell surface will be determined by measuring the fluorescence intensity of the cell pellet suspended in PBS buffer (pH 7.0) using a fluorometer. A standard curve can be prepared by using known amounts of Alexa Fluor 546-conjugated goat anti-mouse IgG. The number of anscaff displayed will be calculated using (RFU$\times 0.945 \times 10^7$)/$1 \times 10^7$ as reported previously. Similarly, the secretion level for the two anScaffs and the different cellulases can be determined. The secretion of anScaff in the medium can be confirmed first by incubating the medium with Avicel for 1 h. After incubation, Avicel is separated by centrifugation and the bound protein after washing three times with PBS buffer is analyzed by SDS-PAGE and Western blot against either the S-tag or C-myc tag. The amount of cellulases produced is analyzed by SDS-PAGE and enzyme assays using procedures that are already in place. After confirming expression, the four different strains are co-cultured and the correct assembly of the adaptor scaffoldins and cellulases onto the cell surface confirmed by immunofluorescence microscopy and the ability to hydrolyze Avicel. Xylanase activity can be measured as described by Bailey et al., 1992).

The disclosure demonstrates a synthetic consortium for surface-display of a complex cellulosome by combining cells displaying the anchoring and adaptor scaffoldins with cells secreting the dockerin-borne cellulases. The modular nature of the cellulosome and great diversity of cellulases, and the availability of gene fusion technology provide almost unlimited number of combinations of enzymes and ways to incorporate them into artificial cellulosome as designed to optimize their activities to approach or even surpass the natural cellulosome. It has been shown by Fierobe et al (2002; 2005) that cellulosomes containing different cellulases have significantly different abilities for cellulose hydrolysis; even the same cellulases fused to different dockerins can result in celluosomes with substantially different hydrolysis efficiencies (up to 2-3 fold), suggesting the order of enzymes on the cellulosome can directly impact the overall activity. In an effort to create the most efficient combination for cellulose hydrolysis, dockerin replacement among the enzymes can be revised and modulated. All possible dockerin combinations will be created and the resulting activity of the cellulosomes can be compared for hydrolysis. Overlap-extension PCR can be used for replacements of the dockerins. Briefly the reverse primers for the region coding for the C-terminal part of the catalytical domain of each cellulase can be overlapped with the forward primers for the region coding for the N-terminal part of the dockerin domain. After several runs of denature, aligning, and extension in PCR the resultant overlapping fragments will be mixed and combined fragment will be synthesized by using external primers. DNS method as described herein can be used for evaluating the efficiencies of the different cellulosome complexes and their synergy effects as well as glucose liberation.

After optimizing the activity of the cellulosome, the ability of the consortium to hydrolyze Avicel and the corresponding ethanol production can be analyzed. Initially, growth rates of each individual strain are determined to check for any substantial difference in cell growth. Samples are taken periodically for monitoring the expression level, reducing sugar, intermediates, and cell growth. One can coordinate the four different cell populations so that maximum synergy can be obtained and no enzyme represents a limiting step. This can be ensured by using cellulose hydrolysis and following the hydrolysis products by a carbohydrate analysis method established on a Dionex High-pH Ion-Exchange Chromatograph System with electrochemical detector, which detects oligosaccharides (cellobiose, glucose and the like), allowing one to pinpoint limiting enzyme activities (if any) (endo/exo glucanases or β-glucosidase). A coordinated gene expression system leads to the detection of only glucose, whereas accumulations of other products indicate the level of secreted enzymes (or cell population) should be adjusted by varying the gene copy number.

The engineered strains can be evaluated for cellulose hydrolysis and ethanol production under different conditions such as resting and growth conditions in SDC medium. Both small and large-scale (shaker flask/one liter bioreactor) studies can be performed. In resting cell experiments, cells are grown aerobically using glucose as the carbon source. Cells are then washed and used in cellulose anaerobic hydrolysis. Enzyme activity, the integrity of cellulosome, hydrolysis products, glucose, ethanol will be monitored using methods described herein. In studies carried out in a fermentor, a mild agitation can be used to promote mixing of solid cellulose material with cells. Once optimized industrial yeast fermentation process may be used. Different cellulose concentrations can also be used. The rate of glucose generation will be estimated from the experiments and compared to those without cellulosome on the cell surface (but with comparable enzyme expression levels). In studies under growing conditions, the cells will be provided cellulose as the sole carbon source, and other nutrients necessary for growth. Anaerobic conditions are maintained. Cell biomass, enzyme activities, cellulosome integrity, any possible accumulated hydrolysis products including glucose, and ethanol are measured.

The disclosure provides yeast strains for direct fermentation of cellulose to ethanol, eliminating the need for use of purified cellulases. The methods and compositions of the disclosure provide abundant, low-cost, agriculture residue to be used as raw material for ethanol production. The increased production of ethanol not only reduces pollution to the environment but also the need for imported petroleum as transportation fuel. Collectively, the benefits from the invention include at least efficient, economical, and environmentally friendly conversion of biomass.

Current biofuel production processes are exclusively based upon the soluble enzyme approach, the less efficient model utilized by aerobic microbes. The construction of cellulosomes on the cell surface as described herein departs from the current model of enzymatic hydrolysis. A difference lies in the extent of synergism. While the secretion or co-display of cellulases (without the cellulosome structure) permits a synergistic use of these enzymes to some extent, both follow the model of aerobic organisms in cellulose hydrolysis. As exemplified by *Trichoderma. reesei*, this model requires the production of abundant enzymes without needing to maximize the efficiency and synergism. Since ethanol production is carried out anaerobically, the limited amount of enzyme production makes the high coordination of different enzyme components necessary to maximize the synergy and efficiency.

As used herein, the term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

As used herein, the term "polynucleotide" refers to a polymer of nucleic acid bases such as deoxyribonucleic acid (DNA), and, where appropriate, ribonucleic acid (RNA). The term should also be understood to include, analogs of either RNA or DNA made from nucleotide analogs, and, as applicable to the embodiment being described, single (sense or antisense) and double-stranded polynucleotides.

The term "carbon source" generally refers to a substrate or compound suitable to be used as a source of carbon for bacterial or simple eukaryotic cell growth. Carbon sources may be in various forms, including, but not limited to polymers, carbohydrates such as cellulosic material including celluloo-ligosaccharides and lignocellulose, acids, alcohols, aldehydes, ketones, amino acids, peptides, etc. These include, for example, various monosaccharides such as glucose, oligosaccharides, polysaccharides, saturated or unsaturated fatty acids, succinate, lactate, acetate, ethanol, and the like, or mixtures thereof.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway associated with a engineered microorganism as described herein. A "biomass derived sugar" includes, but is not limited to, molecules such as glucose, sucrose, mannose, xylose, and arabinose. Exemplary substrate sources include alfalfa, corn stover, crop residues, debarking waste, forage grasses, forest residues, municipal solid waste, paper mill residue, pomace, sawdust, spent grains, spent hops, switchgrass, and wood chips.

As used herein, the terms "gene" and "recombinant gene" refer to an exogenous nucleic acid sequence which is transcribed and (optionally) translated. Thus, a recombinant gene can comprise an open reading frame encoding a polypeptide. In such instances, the sequence encoding the polypeptide may also be referred to as an "open reading frame".

"Transcriptional regulatory sequence" is a generic term used throughout the specification to refer to DNA sequences, such as initiation signals, enhancers, and promoters, which induce or control transcription of a gene or genes with which they are operably linked.

"Operably linked" means that a gene and transcriptional regulatory sequence(s) are connected in such a way as to permit expression of the gene in a manner dependent upon factors interacting with the regulatory sequence(s).

"Exogenous" means a polynucleotide or a peptide that has been inserted into a host cell. An exogenous molecule can result from the cloning of a native gene from a host cell and the reinsertion of that sequence back into the host cell. In most instances, exogenous sequences are sequences that are derived synthetically, or from cells that are distinct from the host cell.

The terms "host cells" and "recombinant host cells" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "reporter gene" is a gene whose expression may be assayed; reporter genes may encode any protein that provides a phenotypic marker, for example: a protein that is necessary for cell growth or a toxic protein leading to cell death, e.g., a protein which confers antibiotic resistance or complements an auxotrophic phenotype; a protein detectable by a colorimetric/fluorometric assay leading to the presence or absence of color/fluorescence; or a protein providing a surface antigen for which specific antibodies/ligands are available.

The term "biosynthetic pathway", also referred to as "metabolic pathway", refers to a set of anabolic or catabolic biochemical reactions for converting (transmuting) one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

As used herein, the term "metabolic pathway" includes catabolic pathways and anabolic pathways both natural and engineered i.e. synthetic. Anabolic pathways involve constructing a larger molecule from smaller molecules, a process requiring energy. Catabolic pathways involve breaking down of larger molecules, often releasing energy. An anabolic pathway is referred to herein as "a biosynthetic pathway."

Biofuel is any fuel that derives from biomass-organisms, such as plants, fermentation waste, or metabolic byproducts, such as manure from cows. It is a renewable energy source, unlike other natural resources such as petroleum, coal and nuclear fuels. Agricultural products specifically grown for use as biofuels and waste from industry, agriculture, forestry, and households—including straw, lumber, manure, sewage, garbage and food leftovers—can be used for the production of bioenergy.

Cellulose is a polymer polysaccharide carbohydrate, of beta-glucose. It forms the primary structural component of plants and is not digestible by humans. Cellulose is a common material in plant cell walls and was first noted as such in 1838. Cellulose is the most abundant form of living terrestrial biomass (Crawford, R. L. 1981. Lignin biodegradation and transformation, John Wiley and Sons, New York). Cellulose is also the major constituent of paper. Cellulose monomers (beta-glucose) are linked together through 1,4 glycosidic bonds.

A polynucleotide, polypeptide, or peptides may have a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), Mol. Biol. 215:403-10.

Exemplary polynucleotide and polypeptides are provided herein. One of skill in the art will recognize that minor modification (e.g., conservative substitutions and the like) can be made to the polypeptide without destroying the biological/enzymatic activity of the polypeptide. Such modification, variation and the like are within the skill in the art as it relates to molecular biology. Screening for activity of such modified polypeptides is described herein. Accordingly, the disclosure encompass polynucleotide and polypeptides having at least 60%, 70%, 80%, 90%, 95%, 98% or 99% identity to a sequence as set forth herein and having a biological activity similar to the wild-type molecule.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons.

Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for S. cerevisiae and mammals are UAA and UGA, respectively. The typical stop codon for monocotyledonous plants is UGA, whereas insects and E. coli commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

The recombinant yeast cellulosome of the disclosure can be engineered based upon the cellulosic material to be metabolized. For example, different cellulases and other enzymes may be engineered into a cellulosome pathway depending upon the source of substrate. Exemplary substrate sources include alfalfa, corn stover, crop residues, debarking waste, forage grasses, forest residues, municipal solid waste, paper mill residue, pomace, sawdust, spent grains, spent hops, switchgrass, and wood chips. Some substrate sources can have a larger percentage of cellulose compared to other source, which may have a larger percentage of hemicellulose. A hemicellulose substrate comprises short, branched chains of sugars and can comprise a polymer of five different sugars. Hemicellulose comprises five-carbon sugars (e.g., D-xylose and L-arabinose) and six-carbon sugars (e.g., D-galactose, D-glucose, and D-mannose) and uronic acid. The sugars are typically substituted with acetic acid. Hemicellulose is relatively easy to hydrolyze to its constituent sugars. When hydrolyzed, the hemicellulose produces xylose (a five-carbon sugar) or six-carbon sugars from hardwoods or softwoods, respectively.

In some instances the feedstock can be pretreated using heat, acid treatment or base treatment. Possible pre-treatments include the use of dilute, acid, steam explosion, ammonia fiber explosion (AMFE), organic solvents (BioCycle, May 2005 News Bulletin, and see: Ethanoi from Cellulose: A General Review, P. Badger, p. 17-21 in J. Janick and A. Whipkey (eds.), Trends in New Crops and Uses, ASHS Press, 2002). Typically the pretreatment will be biocompatible or neutralized prior to contact with a recombinant microorganism of the disclosure.

Proteins or polypeptides having the ability to convert the hemicellulose components into carbon sources that can be used as a substrate for biofuel production includes, for example, cellobiohydrolases (Accessions: AAC06139, AAR87745, EC 3.2.1.91, 3.2.1.150), cellulases (E.C. 3.2.1.58, 3.2.1.4, Accessions: BAA12070, BAB64431); chitinases (E.C. 3.2.1.14, 3.2.1.17, 3.2.1.-, 3.2.1.91, 3.2.1.8, Accessions: CAA93150, CAD12659), various endoglucanases (E.C. 3.2.1.4, Accessions: BAA92430, AAG45162, P04955, AAD39739), exoglucanases (E.C. 3.2.1.91, Accessions: AAA23226), lichenases (E.C. 3.2.1.73, Accessions: P29716), mannanases (E.C. 3.2.1.4, 3.2.1.-, Accessions: CAB52403), pectate lyases (E.C. 4.2.2.2, Accessions: AAG59609), xylanase (E.C. 3.2.1.136, 3.2.1.156, 3.2.1.8, Accessions: BAA33543, CAA31 109) and silase (E.C. 3.2.2.-, 2.7.7.7, Accessions: CQ80097S).

Cellulases are a class of enzymes produced chiefly by fungi, bacteria, and protozoans that catalyze the hydrolysis of cellulose. However, there are also cellulases produced by other types of organisms such as plants and animals. Several different kinds of cellulases are known, which differ structurally and mechanistically. The EC number for cellulase enzymes is E.C.3.2.1.4. Assays for testing cellulase activity are known in the art.

Polypeptides having xylanase activity are useful for including in synthetic cellulosomes. Xylanases is the name given to a class of enzymes which degrade the linear polysaccharide beta-1,4-xylan into xylose, thus breaking down hemicellulose. The EC number for xylanase enzymes is E.C. 3.2.1.136, 3.2.1.156, 3.2.1.8. Assays for testing xylanase activity are known in the art.

Scaffold or structure polypeptides refer to peptides that do not have enzymatic activity, but rather play a role as a building block. For example, scaffold or structure polypeptides as used herein include scaffoldin, cohesion, and cellulose binding polypeptides useful for generating the cellulosome structure for binding of enzyme(s) to the host cell surface, or bind the cellulosic material degrading enzyme(s) to the cellulosic material carbon source. In one example, a recombinant cellulosome of the disclosure can comprise a recombinant scaffold polypeptide and/or a recombinant enzymatic polypeptide. For example, a synthetic cellulosome can have a cellulosic material degrading enzyme domain, and one or more structural domains. Depending on the structural peptide domain the synthetic cellulosome will bind to the carbon source and serve to place the cellulosic material degrading enzyme activity in close physical proximity to the carbon source. In other examples the synthetic cellulosome will have peptide sequences that bind the synthetic cellulosome to the host cell surface function to place the cellulosic material degrading enzyme activity in close proximity to the cell surface.

Yeast of the disclosure are engineered to convert cellulosic material to a biofuel, such as ethanol, by engineering them to produce both a synthetic cellulosome and cellulose degrading enzymes. Multiple recombinant yeast can be co-cultured to generate the cellulosome, each of a plurality of recombinant yeast producing one or more, but not all, the elements of a function cellulosome.

One of ordinary skill in the art will appreciate that there are a variety of synthetic cellulosomes that can be made, for example, comprising a variety of degradation enzymes for a specific cellulose or hemicelluloses containing material, a variety of associated scaffoldin and cohesion molecules to generate a recombinant cellulosome having a desired efficiency or pathway of degrading enzymes provided herein.

A microorganism (e.g., a yeast) are engineered to express the synthetic cellulosome by constructing a vector containing a scaffoldin domain, a Carbohydrate Binding Domain (CBM), and one or more cellulosic material-degrading enzymes that have been fused with cohesin domains. In one embodiment, a plurality of different recombinant micoorganisms are generated each expressing a desired element of a cellulosome. For example, a first recombinant yeast can comprise a polynucleotide encoding a heterologous anchoring protein, a second recombinant yeast comprising a polynucleotide encoding a soluble scaffoldin unit comprising a plurality of cohesion units and a cellulose binding domain, and a third recombinant yeast comprising a polynucleotide encoding an enzyme (e.g., a cellulose or other degradation enzyme) linked to a dockerin subunit. The cells can be recombinant engineered to produce the elements of the cellulosome, wherein a function cellulusome is produced and function in culture.

The following examples are intended to illustrate but not limit the disclosure. While they are typical of those that might be used, other procedures known to those skilled in the art may alternatively be used.

EXAMPLES

Strains, Plasmids, and Media

*Escherichia coli* strain JM109 [endA1 recA1 gyrA96 thi hsdR17 (rK$^-$mK$^+$) relA1 supE44 Δ(lac-proAB)] was used as the host for genetic manipulations. *E. coli* BL21 (DE3) [F-ompT gal hsdSB (rB- mB-) dcm lon λDE3] was used as the production host for cellulase expression. *S. cerevisiae* strain EBY100 [MATa AGA1::GAL1-AGA1::URA3 ura3-52 trp1 leu2-1 his3-200 pep4::HIS3 prb1-1.6R can1 GAL] was used for surface display of scaffoldins. All *E. coli* cultures were grown in Luria-Bertani (LB) medium (10.0 g/liter tryptone, 5.0 g/liter yeast extract, 10.0 g/liter NaCl) supplemented with either 100 μg/ml ampicillin or 50 μg/ml kanamycin. All yeast cultures were grown in SDC medium (20.0 g/liter dextrose, 6.7 g/liter yeast nitrogen base without amino acids, 5.0 g/liter Casamino Acids).

To display scaffoldins, a gene fragment coding for a scaffoldin containing three cohesins from *C. cellulolyticum, C. thermocellum,* and *R. flavefaciens* and one CBD was amplified with plasmid pETscaf6 as the template with forward primer F1NdeI (5'-TATAGCTAGCGGCGATTCTCT-TAAAGTTACAGT-3' [the boldface portion is a restriction endonuclease site]) and reverse primer R1SalI (5'-ATAT-GTCGACGTGGTGGTGGTGGTG-3'). The PCR product was then digested and ligated into the surface display vector pCTCON2 to form pScaf-ctf. Similar procedures, except that the reverse primers were changed to RASalI (5'-ATATGTC-GACATCTGACGGCGGTATTGTTGTTG-3') and RBSalI (5'-ATATGTCGACTATATCTCCAACATTTACTCCAC-3'), were used for the construction of pSacf-c and pSacf-ct.

Plasmids pETEc and pETGf, encoding exoglucanase CelE (Ec) and endoglucanase CelG (Gf) of *C. cellulolyticum* fused to the dockerins from *C. cellulolyticum* and *R. flavefaciens*, respectively. Plasmid pETAt, encoding a His6-tagged endoglucanase (CelA) and a dockerin from *C. thermocellum* (At), was obtained by PCR from pCelA with forward primer F2NdeI (5'-ATATCATATGGCAGGTGTGCCTTTTAA-CACAAA-3') and reverse primer R2XhoI (5'-ATATCTC-GAGCTAATAAGGTAGGTGGGG-3'). The amplified fragment was cloned into NdeI-XhoI-linearized plasmid pET24a to form pETAt. Plasmid pBglAf, encoding a His6-tagged dockerin from *R. flavefaciens* fused to a β-glucosidase (BglA) from *C. thermocellum*, was obtained by two-step cloning. First, a gene fragment coding for the His6-tagged dockerin of *R. flavefaciens* was obtained from pETGf by digestion with BamHI and XhoI and ligated into pET24a to form pETDf. The gene fragment of BglA was amplified by PCR from pBglA with forward primer F3NdeI (5'-ATATCATATGT-CAAAGATAACTTTCCCAAAA-3') and reverse primer R3BglII (5'-ATATAGATCT TTAAAAACCGT-TGTTTTTGATTACT-3') and inserted into NdeI-BamHI-linearized pETDf to form pBglAf. A summary of all of the scaffoldins and dockerin-tagged cellulases used in this study is listed in Table 1.

TABLE 1

Scaffoldins and dockerin-tagged cellulases used in this study

| Protein name | Description (from N terminus to C terminus) | Host cell | Tag |
|---|---|---|---|
| Scaf-c | Scaffoldin containing a cohesin from *C. cellulolytica* followed by a CBD | *S. cerevisiae* | c-Myc |
| Scaf-ct | Scaffoldin containing a cohesin from *C. cellulolytica* followed by a CBD followed by a second cohesin from *C. thermocellum* | *S. cerevisiae* | c-Myc |
| Sacf-ctf | Scaffoldin containing a cohesin from *C. cellulolytica* followed by a CBD followed by a second cohesin front *C. thermocellum* and a third cohesin from *R. flavefaciens* | *S. cerevisiae* | c-Myc |
| At | Endoglucanase CelA from *C. thermocellum* fused with its native dockerin | *E. coli* | c-His$_6$ |
| Ec | Exoglucanase CelE from *C. cellulolytica* fused with its native dockerin | *E. coli* | c-His$_6$ |
| Gf | Endoglucanase CelG from *C. cellulolytica* fused with a dockerin from *R. flavefaciens* | *E. coli* | c-His$_6$ |
| BglA | β-Glucosidase BglA from *C. thermocellum* fused with a dockerin from *R. flavefaciens* | *E. coli* | c-His$_6$ |

Figure 3:
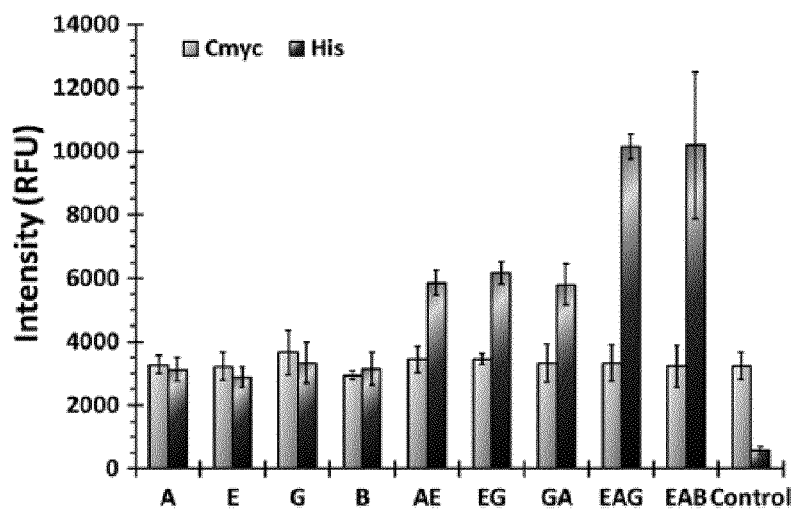
FIG. 3 shows fluorescence intensity of cells either displaying scaffoldin Sacf-ctf or with different combinations of dockerin-tagged cellulases (At [A], Ec [E], and Gf [G]) docked on the displayed Sacf-ctf. Cells were probed with either anti-c-Myc or anti-c-His6 serum and fluorescently stained with goat anti-mouse IgG conjugated with Alexa Fluor 488. Whole-cell fluorescence was determined with a fluorescence microplate reader. Cells displaying only Scaf-ctf were used as controls. RFU, relative fluorescence units.

A plasmid coding for a trifunctional scaffoldin (Scaf-ctf (SEQ ID NO:1 and 2) consisting of an internal CBD flanked by three divergent cohesin domains from *C. thermocellum* (t), *C. cellulolyticum* (c), and *R. flavefaciens* (f) (FIG. 3) was created for surface display. To further demonstrate the specificity of the different dockerin-cohesin pairs, two smaller scaffoldins, (i) Scaf-c containing a cohesin domain from *C. cellulolyticum* followed by a CBD and (ii) Scaf-ct containing an additional cohesin domain from *C. thermocellum* at the C terminus of the CBD, were generated (FIG. 3). The different scaffoldins were displayed on the yeast cell surface by using the glycosylphosphatidyl-inositol (GPI) anchor linked at the N-terminal side of the scaffoldins. A c-Myc tag was added to the C terminus of each scaffoldin to allow detection with antic-Myc serum.

Display of Scaffoldins on the Yeast Cell Surface.

For the display of scaffoldins on the yeast cell surface, yeast cells harboring pScaf-c, pScaf-ct, or pScaf-ctf were precultured in SDC medium for 18 h at 30° C. These precultures were subinoculated into 200 ml SGC medium (20.0 g/liter galactose, 6.7 g/liter yeast nitrogen base without amino acids, 5.0 g/liter Casamino Acids) at an optical density (OD) at 600 nm of 0.1 and grown for 48 h at 20° C.

Expression and Purification of Dockerin-Tagged Cellulases.

E. coli strains expressing At, Ec, and Gf were precultured overnight at 37° C. in LB medium supplemented with appropriate antibiotics. The precultures were subinoculated into 200 ml LB medium supplemented with 1.5% glycerol and appropriate antibiotics at an initial OD of 0.01 and incubated at 37° C. until the OD reached 1.5. The cultures were then cooled to 20° C., and isopropyl-β-D-thiogalactopyranoside (IPTG) was added to a final concentration of 200 µM. After 16 h, cells were harvested by centrifugation (3,000×g, 10 min) at 4° C., resuspended in buffer A (50 mM Tris-HCl [pH 8.0], 100 mM NaCl, 10 mM CaCl2), and lysed with a sonicator. The different cellulases were purified with a His-binding resin (Novagen) at 4° C.

Minicellulosome Assembly on the Yeast Cell Surface.

To assemble the minicellulosomes, either cell lysates containing dockerin-tagged cellulases or purified cellulases were incubated with yeast cells displaying the scaffoldin for 1 h at 4° C. in buffer A. After incubation, cells were washed and harvested by centrifugation (3,000×g, 10 min) at 4° C. and resuspended in the same buffer for further use.

Immunofluorescence Microscopy.

Yeast cells displaying scaffoldins or the minicellulosomes on the surface were harvested by centrifugation, washed with phosphate-buffered saline (PBS; 8 g/liter NaCl, 0.2 g/liter KCl, 1.44 g/liter Na2HPO4, 0.24 g/liter KH2PO4), and resuspended in 250 µl of PBS containing 1 mg/ml bovine serum albumin and 0.5 µg of anti-c-Myc or anti-c-His immunoglobulin G (IgG; Invitrogen) for 4 h with occasional mixing. Cells were then pelleted and washed with PBS before resuspension in PBS plus 1 mg/ml bovine serum albumin and 0.5 µg anti-mouse IgG conjugated with Alexa 488 (Molecular Probes). After incubation for 2 h, cells were pelleted, washed twice with PBS, and resuspended in PBS to an OD at 600 nm of 1. For fluorescence microscopy (Olympus BX51), 5- to 10-_l volumes of cell suspensions were spotted onto slides and a coverslip was added. Images from Alexa 488 were captured with the QCapture Pro6 software. Whole-cell fluorescence was measured with a fluorescence microplate reader (Synergy4; BioTek, VT) at an excitation wavelength of 485 nm and an emission wavelength of 535 nm.

Enzyme Assays.

Carboxymethyl cellulose (CMC) was obtained from Sigma and used as a substrate. Phosphoric acid-swollen cellulose (PASC) was prepared from Avicel PH101 (Sigma) according to the method of Walseth (27). Enzyme activity was assayed in the presence of a 0.3% (wt/vol) concentration of cellulose at 30° C. in 20 mM Tris-HCl buffer (pH 6.0). Samples were collected periodically and immediately mixed with 3 ml of DNS reagents (10 g/liter dinitrosalicylic acid, 10 g/liter sodium hydroxide, 2 g/liter phenol, 0.5 g/liter sodium sulfite). After incubation at 95° C. for 10 min, 1 ml of 40% Rochelle salts was added to fix the color before measurement of the absorbance of the supernatants at 575 nm. Glucose concentration was determined with a glucose HK assay kit from Sigma.

Fermentation.

Fermentation was conducted anaerobically at 30° C. Briefly, yeast cells were washed once with buffer containing 50 mM Tris-HCl (pH 8.0), 100 mM NaCl, and 10 mM CaCl2 and resuspended in SDC medium containing 6.7 g/liter yeast nitrogen base without amino acids, 20 g/liter Casamino Acids, and 10 g/liter PASC as the carbon source. Reducing sugar production and glucose concentration were measured by the methods described above. The amount of residual cellulose was measured by the phenol-sulfuric acid method as described by Dubois et al. Ethanol concentration was measured with a gas chromatograph (model 6890; Hewlett Packard) with a flame ionization detector and an HP-FFTP column.

To probe the surface localization of the scaffoldins, immunofluorescent labeling of cells was carried out using anti-c-Myc sera and Alexa Fluor TM 488 conjugated goat anti-mouse IgG (Molecular Probe) and observed under a fluorescence microscope (Olympus America, Inc., San Diego, Calif.). Cells displaying the scaffoldin domains (1, 2, or 3) on the surface were brightly fluorescence (FIG. 2), while no fluorescence was observed for the control yeast cells. These results demonstrate that a synthetic scaffoldin can be successfully displayed on the surface of a heterologous host (e.g., a yeast).

To test the functionality of the displayed scaffoldins, three different cellulases fused with a corresponding dockerin domain (either c, t, or f) were expressed in E. coli (i.e., an exoglucanase (CelE) from C. cellulolyticum fused to a dockerin domain from the same species (Ec), an endoglucanase (CelG) from C. cellulolyticum fused to a dockerin domain from R. flavefaciens (Gf), and an endoglucanase (CelA) fused to a dockerin domain from C. thermocellum (At) were expressed in E. coli). The plasmids used were: (i) pETEc containing an exoglucanase CelE from C. cellulolytica fused with a dockerin domain from the same species (Ec; see, e.g., SEQ ID NO:3 and 4, Christian Gaudin et al., Journal of Bacteriology, 2000. 182: 1910-1915, incorporated herein by reference); (ii) pETGf containing an endoglucanase CelG from C. cellulolytica fused with a dockerin domain from R. flavefaciens (Gf; see, e.g., SEQ ID NO:5 and 6; Henri-Pierre Fierobe, et al. The Journal of Biological Chemistry. 2005. 280:16325-16334, incorporated herein by reference); and (iii) pETAt containing an endoglucanase CelA fused with a dockerin domain from C. thermocelum (At; see, e.g., SEQ ID NO:7 and 8; Dae-Kyun Chung et al., Biotechnology Letters. 1997, 19:503-506, incorporated herein by reference). A His6 tag was added to the C terminus of each of the dockerin domains for detection of the assembly. Cells displaying scaffoldins on the surface were incubated directly with E. coli cell lysates containing At, Ec, or Gf for 1 h to form the cellulosome complex. The presence of each cellulase-dockerin pair on cells displaying Scaf-ctf was confirmed by immunofluorescence microscopy with the anti-His6 antibody (FIG. 2B).

To demonstrate the specificity of different cohesin-dockerin pairs, similar experiments were performed with cells displaying either Scaf-ct or Scaf-c. In Scaf-ct-displaying cells, fluorescence was detected only in the presence of Ec or At, whereas incubation with Gf did not result in any detectable fluorescence (FIG. 2C). Similarly, in Scaf-c-displaying cells, fluorescence was only observed in the presence of Ec (FIG. 2D). These results confirm that the specificity of the cohesins is preserved even when they are displayed on the cell surface, as only the corresponding dockerin-tagged enzymes are assembled correctly.

Functionality of the Displayed Minicellulosomes.

To demonstrate the functionality of the assembled minicellulosomes, cells expressing Scaf-ctf were first saturated with different combinations of Ec, At, and/or Gf. As depicted in FIG. 3, a similar level of fluorescence was detected from the c-Myc or c-His6 tag when only one dockerin-tagged enzyme was added, indicating the correct 1:1 binding between the cohesin-dockerin pairs. A corresponding increase in fluorescent intensity was observed when an increasing number of enzymes were docked on Scaf-ctf. This result confirms that the correct 1:1 binding ratio of each dockerin-cohesin pair was preserved even when it was assembled into a three-enzyme minicellulosome on the cell surface (FIG. 3).

Figure 4:
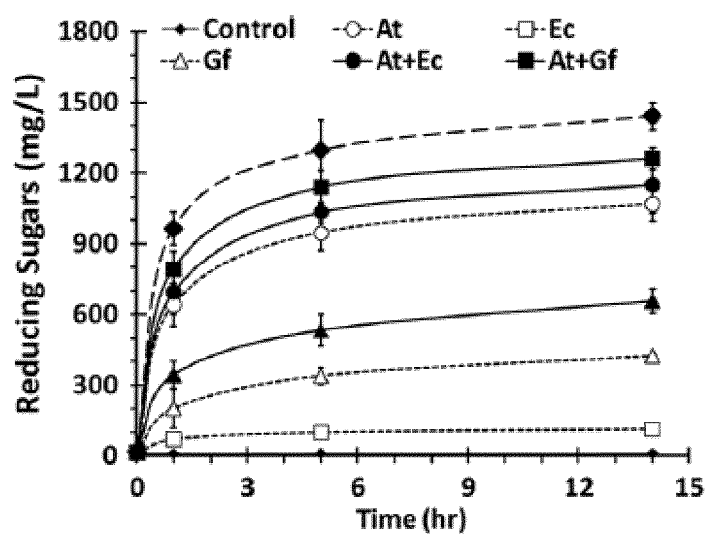
FIG. 4 shows a graph of whole-cell hydrolysis of CMC by different cellulase pairs (CelE-Dc [Ec], CelA-Dt [At], or CelG-Df [Gf]) docked on the displayed Scaf-ctf protein. Cells displaying only Scaf-ctf were used as controls.

Engineered yeast cells docked with different combinations of cellulases were further examined for functionality in cellulose hydrolysis. Cells were resuspended in Tris buffer containing CMC, and the rate of reducing sugar production was determined. As shown in FIG. 4, cells with any one of the three cellulases docked on the surface showed visible differences in cellulose hydrolysis from the control. The endoglucanase At had the highest rate of hydrolysis, followed by Gf and Ec, a trend consistent with the relatively low activity of the exoglucanase CelE on CMC. The rate of CMC hydrolysis increased in an additive fashion when two of the cellulases were docked on the cell surface, and the highest rate of hydrolysis was observed when all three cellulases were assembled. The additive effect on CMC hydrolysis confirms that the recruitment of cellulases to the displayed scafoldin has a very minimum effect on their individual functionality.

Synergistic Effect of Displayed Minicellulosomes.

The synergistic effect on cellulose hydrolysis is an intriguing property of naturally occurring cellulosomes. To test whether the synergistic effect of the minicellulosome structure was preserved when displayed on the yeast cell surface, Avicel hydrolysis was compared with that of purified cellulases. In this case, the amount of each cellulase docked on Scaf-ctf was first determined from the binding experiments. These predetermined amounts of cellulases were then mixed together, and the hydrolysis of Avicel with the cellulase mixture was compared with that of whole cells displaying the functional cellulosome containing the same amount of each cellulase. As shown in Table 2, the level of reducing sugar production was consistently higher for cells displaying the cellulosome, confirming that synergy was indeed maintained. The level of synergy increased from 1.62 to 2.44 when the number of cellulases recruited in the minicellulosome system increased from one to three. This result suggests the potential to further enhance cellulose hydrolysis by increasing the number of displayed cellulases.

TABLE 2

Amounts of reducing sugars released from Avicel after 24 h of incubation at 30° C. either by cells displaying cellulosomes or by the same amount of free enzymes[a]

| Cellulase pair(s) | Amt of reducing sugars (mg/liter) released from: | | Degree of synergy |
|---|---|---|---|
| | Cellulosome | Free enzymes | |
| At | 46.1 | 28.3 | 1.62 |
| At + Ec | 80.1 | 37.6 | 2.13 |
| At + Ec + Gf | 132.3 | 54.2 | 2.44 |

[a]Reactions were conducted either with different cellulase pairs (CelE-Dc [Ec], CelA-Dt [At], or CelG-Df [Gf]) docked on the displayed Scaf-ctf or with the corresponding purified cellulases. The degree of synergy is defined as the amount of sugar released from the cellulosome over the amount of sugar released from free enzymes.

Incorporation of β-Glucosidase into the Minicellulosome.

Since *S. cerevisiae* is unable to transport and utilize oligosaccharides, directing the complete hydrolysis of cellulose to glucose is essential. To achieve this goal, a β-glucosidase (BglA) from *C. thermocellum* tagged with the dockerin from *R. flavefaciens* was constructed. The resulting dockerin-tagged BglA retained the same specificity and docking efficiency as Gf (FIG. 3). FIG. 5 shows the time course of reducing sugar and glucose released from PASC with different enzyme combinations docked on the cell surface. Although 40% of the PASC was hydrolyzed in the presence of the endoglucanase At, 25% of the reducing sugar was further hydrolyzed to glucose.

In comparison, the presence of the exoglucanase Ec not only enhanced reducing sugar production but also increased glucose production threefold. The addition of BglA further improved the rate of glucose liberation, although no difference in reducing sugar formation was observed. This result is very significant, as demonstrated, a functional minicellulosome containing all three exoglucanase, endoglucanase, and β-glucosidase activities can be successfully assembled on the surface of a heterologous host cell. The result also confirms a role of β-glucosidase in achieving a higher conversion of cellulose to glucose. The displayed minicellulosome exhibited synergy in both reducing sugar and glucose liberation compared to that of free enzymes.

Direct Fermentation of Amorphous Cellulose to Ethanol.

Figure 6:
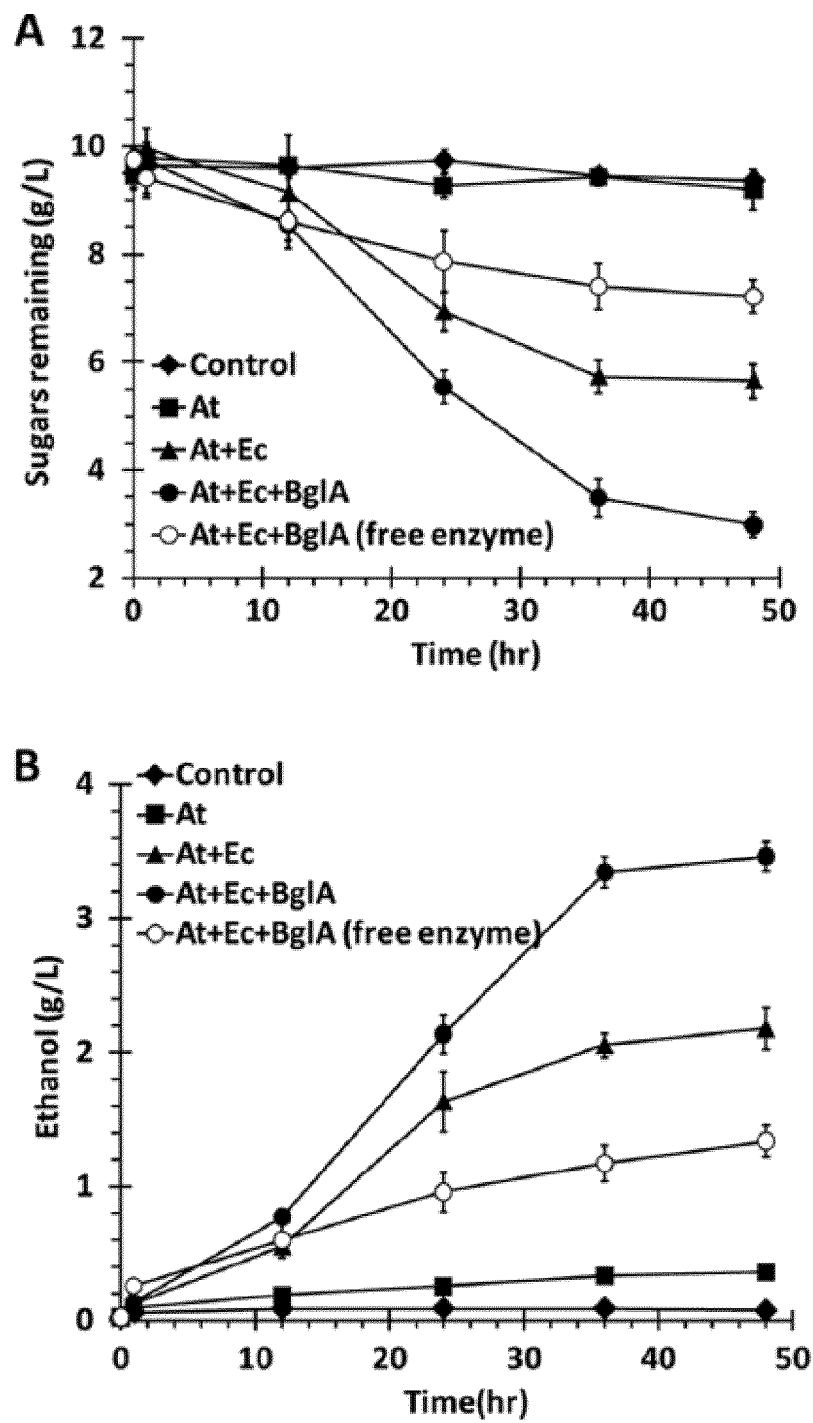
FIG. 6A-B shows time profiles of ethanol production. (A) and cellulose hydrolysis (B) from PASC by control strain EBY100 plus free enzymes and yeast cells displaying functional cellulosomes. Fermentations were conducted either with different cellulase pairs (CelE-Dc [Ec], CelA-Dt [At], or β-glucosidase-Df [BglA]) docked on cells displaying Scaf-ctf or with control strain EBY100 plus the corresponding purified cellulases. Cells displaying only Scaf-ctf were used as controls. The individual enzyme amounts were the same in all cases.
Figure 7:
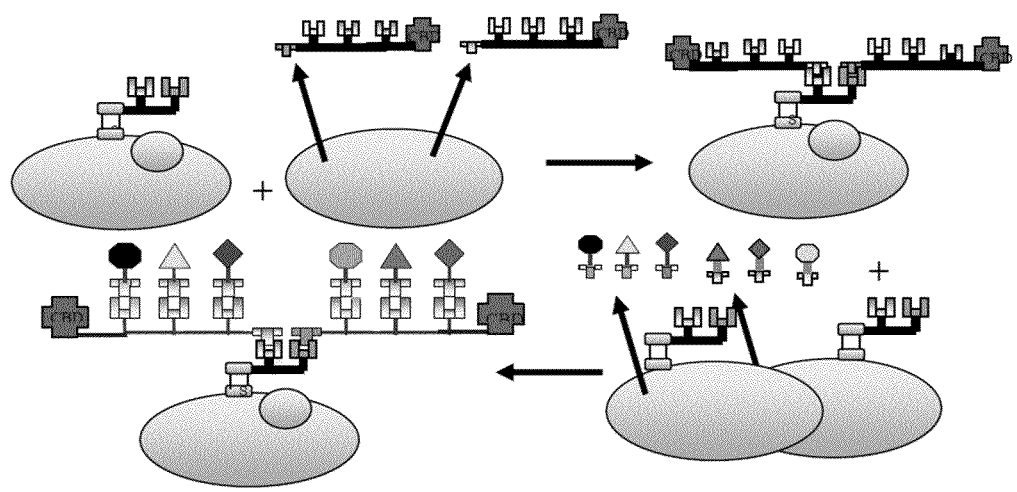
FIG. 7 shows a synthetic consortium for the display of complex cellulosomes.

The ability of ethanol fermentation from PASC was examined by using the scaffoldin-displaying strains docked with different cellulases. As shown in FIG. 6, the increase in ethanol production was accompanied by a concomitant decrease in the total sugar concentration. The levels of ethanol production and PASC hydrolysis were directly correlated with the number of cellulases docked on the cell surface. The maximum ethanol production of cells displaying At, Ec, and BglA was 3.5 g/liter after 48 h; this corresponds to 95% of the theoretical ethanol yield, at 0.49 g ethanol/g sugar consumed. Moreover, the glucose concentrations during the fermentation were below the detection limit. This indicates that all of the glucose produced was quickly consumed, resulting in no detectable glucose accumulation in the medium. The level of ethanol production by cells displaying all three cellulases was higher than that of cells displaying only At and Ec, again confirming the importance of β-glucosidase in the overall cellulose-to-ethanol conversion process. More importantly, the synergistic effect of the minicellulosome was also observed, as the ethanol production by a culture with the same amounts of purified At, Ec, and BglA added to the medium was more than threefold lower.

The feasibility of using secreted cellulases for the direct assembly of functional cellulosome has also been demonstrated. The yeast secretion vector pCEL15 containing the secretion leader sequence MFα1 was used for inserting the gene coding for At. Cells carrying the secretion vector were co-cultured with cells displaying scaff#3 for 24 h. The correct assembly of the secreted At onto the cell surface was again verified by immunofluorescence microscopy. The assembled At remained active as demonstrated by the ability to hydrolyze Avicel. By changing the inoculation densities of the two cultures, different levels of At activity associated with cells and remained in the medium were detected. These results confirm the possibility of fine-tuning the assembly of functional cellulosomes on the cell surface using an engineered consortium of cells performing separate functions.

Overall, the results demonstrated the successful functional assembly of a mini-cellulosome on the yeast surface. The displayed mini-cellulosomes enable the cells to hydrolyze cellulose and grow using cellulose as the sole carbon source. Moreover, the increased cell growth and reducing sugar production with increasing cellulases docked on the surface indicates the potential to further increase the efficiency of cellulose hydrolysis by increasing the number of displayed cellulases via the use of more complex cellulosome structures.

A number of embodiments of the invention have been described. Nevertheless, it will be understood that various modifications may be made without departing from the spirit and scope of the invention. Accordingly, other embodiments are within the scope of the following claims.

Sequence of SCAF6
ATGGGCGATTCTCTTAAAGTTACAGTAGGAACAGCTAATGGTAAGCCTGGCGATACAGTAACAGTTCCTGTTACAT
TTGCTGATGTAGCAAAGATGAAAAACGTAGGAACATGTAATTTCTATCTTGGATATGATGCAAGCCTGTTAGAGGT
AGTATCAGTAGATGCAGGTCCAATAGTTAAGAATGCAGCAGTTAACTTCTCAAGCAGTGCAAGCAACGGAACAATC
AGCTTCCTGTTCTTGGATAACACAATTACAGACGAATTGATAACTGCAGACGGTGTGTTTGCAAATATTAAGTTCA
AATTAAAGAGTGTAACGGCTAAAACTACAACACCAGTAACATTTAAAGATGGTGGAGCTTTTGGTGACGGAACTAT
GTCAAAGATAGCTTCAGTTACTAAGACAAACGGTAGTGTAACGATCGATCCGACCAAGGGAGCAACACCAACAAAT
ACAGCTACGCCGACAAAATCAGCTACGGCTACGCCCACCAGGCCATCGGTACCGACAAACACACCGACAAACACAC
CGGCAAATACACCGGTATCAGGCAATTTGAAGGTTGAATTCTACAACAGCAATCCTTCAGATACTACTAACTCAAT
CAATCCTCAGTTCAAGGTTACTAATACCGGAAGCAGTGCAATTGATTTGTCCAAACTCACATTGAGATATTATTAT
ACAGTAGACGGACAGAAAGATCAGACCTTCTGGTGTGACCATGCTGCAATAATCGGCAGTAACGGCAGCTACAACG
GAATTACTTCAAATGTAAAAGGAACATTTGTAAAAATGAGTTCCTCAACAAATAACGCAGACACCTACCTTGAAAT
AAGCTTTACAGGCGGAACTCTTGAACCGGGTGCACATGTTCAGATACAAGGTAGATTTGCAAAGAATGACTGGAGT
AACTATACACAGTCAAATGACTACTCATTCAAGTCTGCTTCACAGTTTGTTGAATGGGATCAGGTAACAGCATACT
TGAACGGTGTTCTTGTATGGGGTAAAGAACCCGGTGGCAGTGTAGTACCATCAACACAGCCTGTAACAACACCACC
TGCAACAACAAAACCACCTGCAACAACAAAACCACCTGCAACAACAATACCGCCGTCAGATGATCCGAATGCAATA
AAGATTAAGGTGGACACAGTAAATGCAAAACCGGGAGACACAGTAAATATACCTGTAAGATTCAGTGGTATACCAT
CCAAGGGAATAGCAAACTGTGACTTTGTATACAGCTATGACCCGAATGTACTTGAGATAATAGAGATAAAACCGGG
AGAATTGATAGTTGACCCGAATCCTGACAAGAGCTTTGATACTGCAGTATATCCTGACAGAAAGATAATAGTATTC
CTGTTTGCAGAAGACAGCGGAACAGGAGCGTATGCAATAACTAAAGACGGAGTATTTGCTACGATAGTAGCGAAAG
TAAAATCCGGAGCACCTAACGGACTCAGTGTAATCAAATTTGTAGAAGTAGGCGGATTTGCGAACAATGACCTTGT
AGAACAGAGGACACAGTTCTTTGACGGTGGAGTAAATGTTGGAGATATAGGATCCGCCGGTGGTTTATCCGCTGTG
CAGCCTAATGTTAGTTTAGGCGAAGTACTGGATGTTTCTGCTAACAGAACCGCTGCTGACGGAACAGTTGAATGGC
TTATCCCAACAGTAACTGCAGCTCCAGGCCAGACGGTCACTATGCCCGTAGTAGTCAAGAGTTCAAGTCTTGCAGT
TGCTGGTGCGCAGTTCAAGATCCAGGCGGCGACAGGCGTAAGTTATTCGTCCAAGACGGACGGTGACGCTTACGGT
TCAGGCATTGTGTACAATAATAGTAAGTATGCTTTTGGACAGGGTGCAGGTAGAGGAATAGTTGCAGCTGATGATT
CGGTTGTGCTTACTCTTGCATATACAGTTCCCGCTGATTGTGCTGAAGGTACATATGATGTCAAGTGGTCTGATGC
GTTTGTAAGTGATACAGACGGACAGAATATCACAAGTAAGGTTACTCTTACTGATGGCGCTATCATTGTTAAGTAG
Sequence of Ec
ATGCTTGTTGGGGCAGGAGATTTGATTCGAAACCATACCTTTGACAACAGAGTAGGTCTTCCATGGCACGTGGTTG
AATCATACCCTGCAAAGGCAAGTTTTGAAATTACATCTGATGGTAAGTACAAGATAACTGCTCAAAAGATCGGTGA
GGCAGGAAAAGGTGAAAGATGGGATATACAATTCCGTCACAGAGGACTCGCATTGCAACAAGGTCATACTTATACA
GTAAAGTTTACTGTTACTGCTAGCAGAGCTTGTAAAATTTATCCTAAAATAGGTGACCAGGGTGATCCATATGATG
AATACTGGAATATGAATCAACAATGGAATTTCCTGGAATTACAGGCTAATACTCCAAAAACTGTAACTCAGACATT
TACACAGACTAAGGGAGATAAGAAGAACGTTGAATTTGCTTTTCACCTTGCTCCCGATAAAACTACATCTGAGGCA
CAGAATCCAGCAAGTTTCCAACCTATAACATATACTTTTGATGAAATTTATATTCAGGACCCTCAATTTGCAGGAT
ATACTGAAGATCCACCTGAACCTACTAATGTTGTACGTTTGAATCAGGTAGGTTTCTATCCTAATGCTGATAAGAT
TGCAACAGTAGCAACAAGTTCAACAACTCCAATTAACTGGCAGTTGGTTAATAGTACTGGAGCAGCTGTTTTAACA
GGTAAATCAACTGTTAAAGGTGCCGACCGTGCATCAGGTGATAATGTCCATATCATTGATTTCTCTAGTTACACAA
CACCTGGTACCGACTATAAGATAGTAACAGATGTATCAGTAACAAAAGCCGGAGACAATGAAAGTATGAAGTTCAA
TATTGGAGATGACCTTTTTACTCAAATGAAATACGATTCAATGAAGTATTTCTATCACAACAGAAGTGCTATTCCA
ATACAAATGCCATACTGTGATCAATCACAATGGGCACGTCCTGCAGGACACACAACTGATATACTTGCTCCAGATC -continued

```
CAACAAAGGATTACAAGGCTAACTACACACTTGACGTTACAGGTGGTTGGTATGATGCCGGTGACCATGGTAAGTA
TGTTGTTAATGGTGGTATTGCAACCTGGACCGTAATGAATGCATATGAGCGTGCACTACACATGGGTGGAGACACT
TCAGTTGCTCCATTTAAAGACGGTTCTTTAGCAATACCAGAAGCGGAAGTCTATCCTGACATACTGGACGAAGCTC
GTTACCAGCTCATTAACATGAAAACATTATTAAATAGTCAGGTTCCAGCAGGAAAGTATGCGGGTATGGCTCACCA
CAAAGCTCATGACGAACGTTGGACAGCTCTTGCTGTACGTCCCGACCAGGATACAATGAAACGTTGGTTGCAGCCT
CCAAGTACAGCAGCTACATTAAATCTGGCTGCTATTGCTGCACAAAGTTCACGTCTTTGGAAACAGTTTGATTCTG
CTTTCGCAACTAAGTGTTTAACTGCAGCAGAAACTGCTAGGGATGCAGCTGTAGCTCATCCAGAAATATATGCAAC
TATGGAACAGGGTGCCGGTGGTGGAGCATACGGAGACAACTATGTTCTTGATGATTTCTACTGGGCAGCATGTGAA
TTGTATGCAACTACAGGCAGTGACAAGTATTTGAACTACATAAAGAGCTCAAAGCATTATCTCGAAATGCCTACAG
AATTAACAGGCGGTGAGAATACTGGAATTACAGGGGCTTTTGACTGGGGTTGTACAGCAGGTATGGGAACAATAAC
ACTTGCACTTGTACCTACAAAGCTTCCGGCAGCAGATGTTGCTACAGCTAAAGCTAATATTCAAGCTGCAGCTGAT
AAGTTCATATCAATTTCAAAAGCACAAGGCTATGGTGTACCACTAGAAGAAAAGTAATTTCATCTCCTTTTGATG
CATCTGTTGTTAAAGGTTTCCAATGGGGATCAAACTCATTCGTTATTAATGAAGCAATAGTTATGTCATATGCTTA
TGAATTCAGCGATGTTAATGGCACAAAGAATAATAAATATATTAATGGTGCTTTAACAGCAATGGATTACCTCCTC
GGACGTAACCCAAATATTCAAAGCTATATAACTGGTTATGGTGACAACCCACTTGAAAATCCTCATCACCGTTTCT
GGGCATACCAGGCAGACAACACATTCCCAAAACCACCTCCGGGATGTCTGTCAGGAGGACCTAACTCCGGCTTGCA
GGATCCTTGGGTTAAGGGTTCAGGCTGGCAGCCAGGTGAAAGACCTGCTGAAAAATGCTTCATGGACAATATTGAA
TCTTGGTCAACAAACGAAATAACCATCAACTGGAATGCTCCTCTTGTATGGATATCAGCTTACCTTGATGAAAAGG
GGCCAGAGATTGGTGGGTCAGTGACTCCTCCAACTAATTTAGGAGATGTTAACGGCGATGGAAACAAGGATGCATT
GGACTTCGCTGCATTGAAGAAAGCCTTGTTAAGCCAGGATACTTCTACTATAAATGTTGCTAATGCTGATATAAAC
AAAGATGGTTCTATTGATGCAGTTGACTTTGCATTACTCAAATCATTCTTGTTAGGAAAAATCACACAGTGA
```

Sequence of Gf
```
ATGGGAACATATAACTATGGAGAAGCATTACAGAAATCAATAATGTTCTATGAATTCCAGCGTTCGGGAGATCTTC
CGGCTGATAAACGTGACAACTGGAGAGACGATTCCGGTATGAAAGACGGTTCTGATGTAGGAGTTGATCTTACAGG
AGGATGGTACGATGCAGGTGACCATGTGAAATTTAATCTACCTATGTCATATACATCTGCAATGCTTGCATGGTCC
TTATATGAGGATAAGGATGCTTATGATAAGAGCGGTCAGACAAAATATATAATGGACGGTATAAAATGGGCTAATG
ATTATTTTATTAAATGTAATCCGACACCCGGTGTATATTATTACCAAGTAGGAGACGGCGGAAAGGACCACTCTTG
GTGGGGCCCTGCGGAAGTAATGCAGATGGAAAGACCGTCTTTTAAGGTTGACGCTTCTAAGCCCGGTTCTGCAGTA
TGTGCTTCCACTGCAGCTTCTCTGGCATCTGCAGCAGTAGTCTTTAAATCCAGTGATCCTACTTATGCAGAAAAGT
GCATAAGCCATGCAAAGAACCTGTTTGATATGGCTGACAAAGCAAAGAGTGATGCTGGTTATACTGCGGCTTCAGG
CTACTACAGCTCAAGCTCATTTTACGATGATCTCTCATGGGCTGCAGTATGGTTATATCTTGCTACAAATGACAGT
ACATATTTAGACAAAGCAGAATCCTATGTACCGAATTGGGGTAAAGAACAGCAGACAGATATTATCGCCTACAAGT
GGGGACAGTGCTGGGATGATGTTCATTATGGTGCTGAGCTTCTTCTTGCAAAGCTTACAAACAAACAATTGTATAA
GGATAGTATAGAAATGAACCTTGACTTCTGGACAACTGGTGTTAACGGAACACGTGTTTCTTACACGCCAAAGGGT
TTGGCGTGGCTATTCCAATGGGGTTCATTAAGACATGCTACAACTCAGGCTTTTTTAGCCGGTGTTTATGCAGAGT
GGGAAGGCTGTACGCCATCCAAAGTATCTGTATATAAGGATTTCCTCAAGAGTCAAATTGATTATGCACTTGGCAG
TACCGGAAGAAGTTTTGTTGTCGGATATGGAGTAAATCCTCCTCAACATCCTCATCACAGAACTGCTCACGGTTCA
TGGACAGATCAAATGACTTCACCAACATACCACAGGCATACTATTTATGGTGCGTTGGTAGGAGGACCGGATAATG
CAGATGGCTATACTGATGAAATAAACAATTATGTCAATAATGAAATAGCCTGCGATTATAATGCCGGATTTACAGG
TGCACTTGCAAAAATGTACAAGCATTCTGGCGGAGATCCGATTCCAAACTTCAAGGCTATCGAAAAAATAACCAAC
GATGAAGTTATTATAAAGGCAGGTTTGAATTCAACTGGCCCTAACTACACTGAAATCAAGGCTGTTGTTTATAACC
```

-continued

```
AGACAGGATGGCCTGCAAGAGTTACGGACAAGATATCATTTAAATATTTTATGGACTTGTCTGAAATTGTAGCAGC
AGGAATTGATCCTTTAAGCCTTGTAACAAGTTCAAATTATTCTGAAGGTAAGAATACTAAGGTTTCCGGTGTGTTG
CCATGGGATGTTTCAAATAATGTTTACTATGTAAATGTTGATTTGACAGGAGAAAATATCTACCCAGGCGGTCAGT
CTGCGTGCAGACGAGAAGTTCAGTTCAGAATTGCCGCACCACAGGGAAGAAGATATTGGAATCCGAAAATGATTT
CTCATATGATGGATTACCAACCACCAGTACTGTAAATACGGTTACCAACATACCTGTTTATGATAACGGCGTAAAA
GTATTTGGTAACGAACCCGCAGGTGGATCAGAACCCGGCACAAAGCTCGTTCCTACATGGGCGATACAAACTGCG
ACGGCGTTGTAAATGTTGCTGACGTAGTAGTTCTTAACAGATTCCTCAACGATCCTACATATTCTAACATTACTGA
TCAGGGTAAGGTTAACGCAGACGTTGTTGATCCTCAGGATAAGTCCGGCGCAGCAGTTGATCCTGCAGGCGTAAAG
CTCACAGTAGCTGACTCTGAGGCAATCCTCAAGGCTATCGTTGAACTCATCACACTTCCTCAATGA
```

Sequence of At
```
ATGGCAGGTGTGCCTTTTAACACAAAATACCCCTATGGTCCTACTTCTATTGCCGATAATCAGTCGGAAGTAACTG
CAATGCTCAAAGCAGAATGGGAAGACTGGAAGAGCAAGAGAATTACCTCGAACGGTGCAGGAGGATACAAGAGAGT
ACAGCGTGATGCTTCCACCAATTATGATACGGTATCCGAAGGTATGGGATACGGACTTCTTTTGGCGGTTTGCTTT
AACGAACAGGCTTTGTTTGACGATTTATACCGTTACGTAAAATCTCATTTCAATGGAAACGGACTTATGCACTGGC
ACATTGATGCCAACAACAATGTTACAAGTCATGACGGCGGCGACGGTGCGGCAACCGATGCTGATGAGGATATTGC
ACTTGCGCTCATATTTGCGGACAAGTTATGGGGTTCTTCCGGTGCAATAAACTACGGGCAGGAAGCAAGGACATTG
ATAAACAATCTTTACAACCATTGTGTAGAGCATGGATCCTATGTATTAAAGCCCGGTGACAGATGGGGAGGTTCAT
CAGTAACAAACCCGTCATATTTTGCGCCTGCATGGTACAAAGTGTATGCTCAATATACAGGAGACACAAGATGGAA
TCAAGTGGCGGACAAGTGTTACCAAATTGTTGAAGAAGTTAAGAAATACAACAACGGAACCGGCCTTGTTCCTGAC
TGGTGTACTGCAAGCGGAACTCCGGCAAGCGGTCAGAGTTACGACTACAAATATGATGCTACACGTTACGGCTGGA
GAACTGCCGTGGACTATTCATGGTTTGGTGACCAGAGAGCAAAGCAAACTGCGATATGCTGACCAAATTCTTTGC
CAGAGACGGGCAAAAGGAATCGTTGACGGATACACAATTCAAGGTTCAAAAATTAGCAACAATCACAACGCATCA
TTTATAGGACCTGTTGCGGCAGCAAGTATGACAGGTTACGATTTGAACTTTGCAAAGGAACTTTATAGGGAGACTG
TTGCTGTAAAGGACAGTGAATATTACGGATATTACGGAAACAGCTTGAGACTGCTCACTTTGTTGTACATAACAGG
AAACTTCCCGAATCCTTTGAGTGACCTTTCCGGCCAACCGACACCACCGTCGAATCCGACACCTTCATTGCCTCCT
CAGGTTGTTTACGGTGATGTAAATGGCGACGGTAATGTTAACTCCACTGATTTGACTATGTTAAAAAGATATCTGC
TGAAGAGTGTTACCAATATAAACAGAGAGGCTGCAGACGTTAATCGTGACGGTGCGATTAACTCCTCTGACATGAC
TATATTAAAGAGATATCTGATAAAGAGCATACCCCACCTACCTTATTAG
```

---

What is claimed is:

1. A culture comprising:
   a first recombinant yeast strain comprising an anchoring scaffoldin (anScaff);
   a second recombinant yeast strain comprising a secreted adaptor scaffoldin comprising a plurality of cohesion domains and at least one cellulose binding domain (CBD); and
   at least one recombinant yeast strain comprising a plurality of secreted dockerin-tagged cellulases.

2. The culture of claim 1, further comprising culturing the yeast strains under conditions wherein the anchoring scaffoldin, the adaptor scaffoldin comprising the cohesion domains and the plurality of dockerin-tagged cellulases associate to generate an engineered cellulosome.

3. The culture of claim 1, wherein the cellulases are selected from endoglucanases, exoglucanases, β-glucosidase, and xylanase.

4. The culture of claim 1, wherein the dockerin-tagged cellulase is engineered to comprise a leader sequence for secretion of the dockerin-tagged cellulase.

5. The culture of claim 4, wherein the leader sequence comprises an MFβ1 leader sequence.

6. The culture of claim 1, wherein the first strain and second strain are the same.

7. The culture of claim 1, wherein the first recombinant yeast strain comprises a heterologous polynucleotide encoding an anchoring scaffoldin.

8. The culture of claim 1, wherein the second recombinant yeast strain comprises a heterologous polynucleotide encoding a secreted adaptor scaffoldin comprising a plurality of cohesion domains and at least one cellulose binding domain (CBD).

9. The culture of claim 1, wherein the at least one recombinant yeast strain comprises at least one heterologous polynucleotide encoding a secreted dockerin-tagged cellulase.

10. The recombinant yeast strain of claim 8, wherein at least one of cohesion domains is derived from *C. cellulolyticum*.

11. The recombinant yeast strain of claim 8, wherein the heterologous polynucleotide comprises at least six cohesion domains.

12. The recombinant yeast strain of claim 9, wherein at least one of the heterologous polynucleotides encoding a secreted dockerin-tagged cellulase is derived from *C. cellulolyticum*.

13. The recombinant yeast strain of claim 9, wherein the cellulase is selected from endoglucanase, a cellobiohydrolase, a cellulase, a β-glucosidase, a xylanase, a β-xylosidase, a mannanase, a pectate lyase, a silase, a lichenase, and/or a exonuclease.

14. The recombinant yeast strain of claim 9, wherein the cellulase is selected from endoglucanase, exoglucanase, β-glucosidase, and xylanase.

15. The culture of claim 1, wherein at least one of the cohesion domains is derived from *C. cellulolyticum*.

16. The culture of claim 1, wherein at least one of the secreted dockerin-tagged cellulases is derived from *C. cellulolyticum*.

17. The culture of claim 1, wherein the cellulases are selected from endoglucanases, cellobiohydrolases, cellulases, β-glucosidases, xylanases, β-xylosidases, mannanases, pectate lyases, silases, lichenases, and/or a exonucleases.

* * * * *